United States Patent
Hesse et al.

[11] Patent Number: 5,756,733
[45] Date of Patent: May 26, 1998

[54] VITAMIN D AMIDE DERIVATIVES

[75] Inventors: Robert Henry Hesse, Winchester; Sundara Katugam Srinivasasetty Setty, Cambridge; Malathi Ramgopal, Andover, all of Mass.

[73] Assignee: Research Institute for Medicine and Chemistry, Cambridge, Mass.

[21] Appl. No.: 532,799

[22] PCT Filed: May 6, 1994

[86] PCT No.: PCT/GB94/00975

§ 371 Date: Jan. 5, 1996

§ 102(e) Date: Jan. 5, 1996

[87] PCT Pub. No.: WO94/26707

PCT Pub. Date: Nov. 24, 1994

[30] Foreign Application Priority Data

May 7, 1993 [GB] United Kingdom ............... 9309422

[51] Int. Cl.[6] ............... C07D 265/30; C07D 211/06; C07C 401/00; C07C 733/00
[52] U.S. Cl. ............... 544/164; 544/174; 546/205; 552/653; 564/188
[58] Field of Search ............... 564/188; 552/653; 544/174, 164; 546/205

[56] References Cited

FOREIGN PATENT DOCUMENTS

WO-A-91 09841 7/1991 WIPO.
WO-A-93 09093 5/1993 WIPO.

*Primary Examiner*—Alan L. Rotman
*Assistant Examiner*—Raymond Covington
*Attorney, Agent, or Firm*—Bacon & Thomas

[57] ABSTRACT

The invention relates to novel 1α-hydroxy vitamin D derivatives and their 20-epi analogues, comprising compounds of general formula (I)

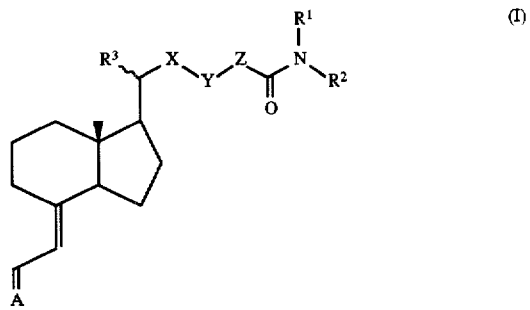

where $R^1$ and $R^2$, which may be the same or different, each represents a hydrogen atom or an aliphatic, cycloaliphatic, araliphatic or aryl group or together with the nitrogen atom to which they are attached form a heterocyclic group; $R^3$ represents a methyl group having α- or β-configuration; X represents a valence bond or a $C_{1-2}$alkylene group; Y represents —O—, —S—, —$CH_2$— or —NR— where R is a hydrogen atom or an organic group; Z represents a valence bond or a $C_{1-3}$alkylene group; and A= represents a cyclohexylidene moiety characteristic of the A-ring of a 1α-hydroxylated vitamin D or analogue thereof, with the proviso that when —X—Y—Z— together represent an alkylene group containing up to 4 carbon atoms A= does not carry an exocyclic methylene group at the 10-position. Active compounds of the invention exhibit cell modulating activity while exhibiting a substantial lack of calcemic effect.

14 Claims, No Drawings

VITAMIN D AMIDE DERIVATIVES

This application is a 371 of PCT/GB94/00975 filed May 6, 1994.

This invention relates to novel vitamin D analogues, more particularly to 1α-hydroxy vitamin $D_3$ analogues having a modified side chain at the 17-position and exhibiting cell modulating activity.

Vitamin $D_3$, which has the formula

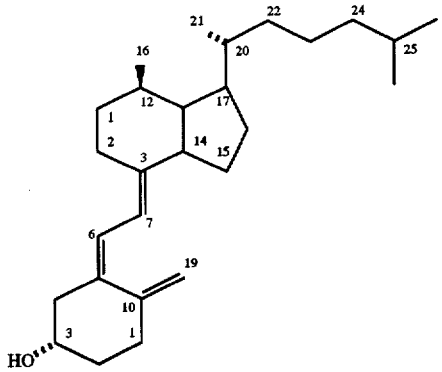

is well known to play a vital role in the metabolism of calcium, by promoting intestinal absorption of calcium and phosphorus, maintaining adequate serum levels of calcium and phosphorus and stimulating mobilisation of calcium from the bone fluid compartment in the presence of parathyroid hormone.

About 20 years ago it was learned that the D vitamins undergo hydroxylation in vivo, hydroxylation at the 25-position occurring in the liver and hydroxylation at the 1α-position occurring in the kidney, the resulting 1α,25-dihydroxy metabolite being the biologically active material. This discovery led to the synthesis of many analogues of vitamin D, evaluation of which indicated that hydroxyl groups at the 1α-position and at either the 24R- or the 25-position were essential for a compound or metabolite thereof to exhibit a substantial effect on calcium metabolism. While, as indicated above, such hydroxyl groups will normally ultimately be introduced in vivo, hydroxylation at the 24R- or 25-position occurring rather more readily than at the 1α-position, the use of vitamin D analogues already so hydroxylated has proved of substantial advantage by virtue of their enhanced levels of activity and their rapidity of action and subsequent elimination from the body. It will be appreciated that 1α-hydroxylated vitamin D derivatives are of especial benefit to patients suffering from renal failure.

Examples of hydroxylated vitamin D analogues in current use include the natural metabolite 1α,25-dihydroxy vitamin $D_3$ and 1α-hydroxy vitamin $D_3$ (which is readily 25-hydroxylated in vivo). Other reportedly promising compounds include 1α,24R-dihydroxy vitamin $D_3$, $D_2$ analogues of the above compounds and 1α,25-dihydroxy analogues carrying fluorine atoms at the 24-, 26- and/or 27-positions (see De Luca and Schnoes, Ann. Rev. Biochem. (1983), 52, pp 411–439 and De Luca et al., Top. Curr. Chem. (1979), 83, pp 1–65).

More recently it has been learned that the natural metabolite 1α,25-dihydroxy vitamin $D_3$ has additional effects on cellular metabolism. These cell modulating effects include stimulation of cell maturation and differentiation (Tanaka et al., Biochem. J. (1982), 204, pp 713–719; Amento et al., J. Clin. Invest. (1984), 73, pp 731–739; Colston et al., Endocrinology (1981), 108, pp 1083–1086; Abe et al., Proc. Nat. Acad. Sci. (1981), 78, pp 4990–4994) and immunosuppressive effects (e.g. inhibition of interleukin II production) (Rigby, Immunology Today (1988), 9, pp 54–58).

Still more recently, an immunopotentiating effect of 1α,25-dihydroxy vitamin $D_3$ has been observed, the compound having been found to stimulate the production of bactericidal oxygen metabolites and the chemotactic response of leukocytes (see, for example, Cohen et al., J. Immunol. (1986), 136, pp 1049–1053). It is well known that leukocytes play a major role in the body's defence against various infections (see, for example, Roitt, Brostoff and Male, "Immunology" $2^{nd}$ Ed. (1989), C. V. Mosby, St. Louis, sec 16.10–16.13 and 17.4–17.5), e.g. by adhering to and engulfing invading organisms (chemotactic response) and/or by producing superoxides and/or other toxic oxygen metabolites. It is known that this response may also be stimulated by mitogens such as the co-carcinogenic phorbal esters and γ-interferon, which are structurally quite different from vitamin D analogues.

By virtue of these effects on cellular metabolism, 1α,25-dihydroxy vitamin $D_3$ in principle has therapeutic potential in such diverse areas as treatment of psoriasis, inflammatory and autoimmune diseases, neoplasias and hyperplasias, as an adjunct in the chemotherapy of infections (inter alia bacterial, viral and fungal), and in other therapeutic modalities in which mononuclear phagocytes are involved. 1α,25-dihydroxy vitamin $D_3$ and 1α-hydroxy vitamin $D_3$ have also been proposed for use in the treatment of hypertension (Lind et al., Acta Med. Scand. (1987), 222, pp 423–427) and diabetes mellitus (Inomata et al., Bone Mineral (1986), 1, pp 187–192), and it has been suggested that 1α,25-dihydroxy vitamin $D_3$ may promote hair growth (Lancet, 4 Mar. 1989, p 478) and may be useful in the treatment of acne (Malloy et al., Tricontinental Meeting for Investigative Dermatology, Washington, 1989).

The potent effects of 1α,25-dihydroxy vitamin $D_3$ and 1α-hydroxy vitamin $D_3$ on calcium metabolism will, however, normally preclude such uses, since dosages at a level sufficient to elicit a desired cell modulating, immunosuppressive or immunopotentiating effect tend to lead to unacceptable hypercalcaemia. This has led to attempts to synthesize new analogues having reduced effects on calcium metabolism but which still exhibit the desired effects on cellular metabolism.

There have been reports of new analogues which exhibit, to at least a moderate degree, this desired separation of activity. Thus the compound MC-903 (calcipotriol), which is a 22,23-unsaturated 1α,24R-dihydroxy vitamin $D_3$ analogue carrying a cyclopropyl group at the 24-position instead of the usual $C_{25}$–$C_{27}$ configuration of the cholestane side chain, and which is under clinical trial for the treatment of psoriasis, is reported to exhibit an effect on cell maturation comparable in magnitude to 1α,25-dihydroxy vitamin $D_3$, while exhibiting a smaller hypercalcaemic effect (Calverley, Tetrahedron (1987), 43, pp 4609–4619; and Holick, Arch. Dermatol. (1989), 125, pp 1692–1696). Similar claims have been made for analogues of 1α,25-dihydroxy vitamin $D_3$, e.g. the 22-oxa (Abe et al., Endocrinology (1989), 124, pp 2645–2647), the 24- and the 26-homo (Ostrem et al., J. Biol. Chem. (1987), 262, pp 14164–14171), the 16-dehydro-23, 24-ethynyl (Zhou et al., Blood (1989), 74, pp 82–93) and the 19-nor-10-dihydro (Perlman et al., Tetrahedron Lett. (1990), pp 1823–1824).

Other analogues of 1α,25-dihydroxy vitamin $D_3$ which have been studied with the aim of achieving enhanced separation of differentiation-inducing activity and hypercalcaemic effect include 23-oxa, 23-thia and 23-aza derivatives (Kubodera et al., Chem. Pharm. Bull. (1991), 39, pp 3221–3224), 22-oxa analogues bearing side chains of different sizes (Kubodera et al., *Chem. Pharm. Bull.* (1992), 40, pp 1494–1499), and 20-epi analogues (Binderup et al., *Biochemical Pharmacology* (1991), 42, pp 1569–1575).

It does not appear possible to deduce from these disclosures either which compounds will exhibit cell modulating activity(or the level of any such activity) or to determine factors which lead to a separation of activities as regards cell modulation and calcium metabolism. Thus, for example, it has been observed that there are no strict relationships between differentiation-inducing activity and side chain length or hydrophilicity.

The majority of results suggest that the presence of a hydroxyl group towards the end of a cholestane-type side chain or homologue thereof is necessary for compounds to show significant cell modulating activity. However, the findings of Ostrem et al. (op. cit.) indicate that analogues having only a short, unsubstituted 17-position side chain (e.g. isopropyl or sec-butyl, as in homo- or bis-homo-pregnanes) exhibit quite substantial differentiation-inducing activity and are more potent than corresponding short side chain compounds bearing a side chain hydroxyl group.

A number of the proposed analogues appear to show cell modulating activity at a similar level to that of 1α,25-dihydroxy vitamin $D_3$, but also appear still to show appreciable effects on calcium metabolism, such activity being attenuated by at most two orders of magnitude relative to that of 1α,25-dihydroxy vitamin $D_3$. This may therefore give rise to cumulative toxicity problems if such compounds are used in long term therapy, particularly where systemic application is required, e.g. for treatment of inflammatory and autoimmune diseases, neoplasias and hyperplasias, or in oral therapy for treatment of psoriasis, and there is thus a continuing need for vitamin D-like compounds which exhibit potent cell modulating activity coupled with a reduced effect on calcium metabolism.

In our copending International Patent Application published as No. WO-A-9309093 there are described a number of 1α-hydroxy vitamin D derivatives and 20-epi analogues thereof in which the 17-position side chain terminates in an optionally N-substituted or N,N-disubstituted carbamoyl group. Such derivatives, while exhibiting minimal effect on calcium metabolism, may have a potent cell modulating effect, for example as evidenced by eliciting cell differentiation and maturation, inhibiting proliferation and/or by activating monocytes (e.g. as estimated by the method of Styrt et al., *Blood* (1986), 67, pp 334–342). Compounds according to the aforesaid International Application have been found to have insignificant effects on serum calcium and phosphorus levels in rats, even when administered in amounts of 100 times a conventional dosage for 1α,25-dihydroxy vitamin $D_3$, and accordingly exhibit an advantageous therapeutic ratio of cell modulating to calcaemic activity.

A further advantage of these compounds is that they have a very low affinity for the intestinal 1α,25-dihydroxycholecalciferol receptor.

The present invention is based on our finding that a wide range of other 1α-hydroxy vitamin D analogues in which the 17-position side chain terminates in an optionally substituted carbamoyl group may also exhibit the desired separation of cell modulating activity and calcaemic effect.

Thus according to one aspect of the invention there are provided compounds of general formula (I)

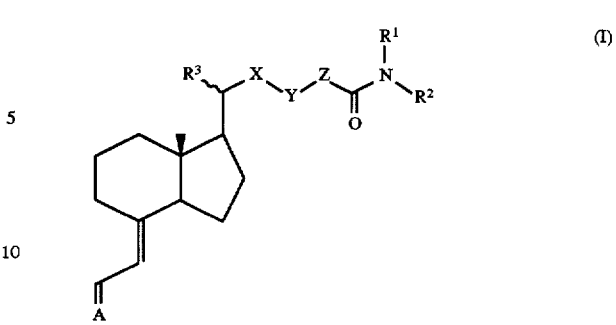

wherein $R^1$ and $R^2$, which may be the same or different, each represent a hydrogen atom or an aliphatic, cycloaliphatic, araliphatic or aryl group or together with the nitrogen atom to which they are attached form a heterocyclic group; $R^3$ represents a methyl group having α- or β-configuration; X represents a valence bond or a $C_{1-2}$ alkylene group; Y represents —O—, —S—, —$CH_2$— or —NR—, where R is a hydrogen atom or an organic group; Z represents a valence bond or a $C_{1-3}$ alkylene group; and A═ represents a cyclohexylidene moiety characteristic of the A-ring of a 1α-hydroxylated vitamin D or analogue thereof, with the proviso that when —X—Y—Z— together represent an alkylene group containing up to 4 carbon atoms A═ does not carry an exocyclic methylene group at the 10-position.

Where $R^1$ and/or $R^2$ in formula (I) represent aliphatic groups these may, for example, be lower (e.g. $C_{1-6}$) alkyl groups such as methyl, ethyl, propyl and butyl groups. Cycloaliphatic groups $R^1$ and/or $R^2$ may, for example, include lower cycloalkyl groups, for example containing 3–8 carbon atoms, e.g. as in cyclopropyl, cyclopentyl and cyclohexyl groups. Araliphatic groups may, for example, include $C_{6-12}$ aryl $C_{1-4}$ alkyl groups such as benzyl or phenethyl. Aryl groups may, for exmaple, include $C_{6-12}$ carbocyclic aryl groups such as phenyl or naphthyl, optionally carrying one or more substituents, for example selected from halo (e.g. chloro or bromo), lower (e.g. $C_{1-4}$) alkyl such as methyl, lower alkoxy (e.g. methoxy), lower alkanoyl (e.g. acetyl), lower alkylamino (e.g. methylamino), di(lower alkyl) amino (e.g. dimethylamino), nitro, carbamoyl and lower alkanoylamino (e.g. acetamido).

Where the group $R^1R^2N$— represents a heterocyclic group this may, for example, contain one or more further heteroatoms selected from O, N and S and may comprise one or more rings, e.g. each having 5 or 6 ring members, for example as in N-attached pyrrolyl, pyrazolyl, imidazolyl, indolyl, indazolyl, purinyl, pyrrolidinyl, imidazolidinyl, pyrazolidinyl, piperidinyl, morpholino, thiazolidinyl or thiamorpholino groups.

Where $R^3$ in formula (I) is a methyl group in the α-configuration the compounds have the 20 R configuration characteristic of natural vitamin D derivatives; where $R^3$ is in the β-configuration the compounds have the 20 S configuration of epi-vitamin D derivatives. It will be appreciated that the invention also embraces mixtures of the two isomers.

Alkylene groups represented by X and Z may, for example, be straight-chained as in methylene, ethylene or (in the case of Z) trimethylene. The total number of carbon atoms present in X and Z is preferably in the range 1–4.

Where Y represents —NR—, organic groups which may be present as R include, for example, lower (e.g. $C_{1-6}$) alkyl such as methyl, ethyl, propyl or butyl; lower (e.g. $C_{3-8}$) cycloalkyl such as cyclopropyl, cyclopentyl or cyclohexyl; lower aralkyl, e.g. $C_{6-12}$ aryl-$C_{1-4}$ alkyl such as benzyl; or lower acyl, e.g. $C_{1-6}$ alkanoyl such as acetyl.

The cyclohexylidene ring represented by A= will normally carry hydroxyl groups or protected derivatives thereof at the 1α- and 3β-positions, and may carry further substituents, e.g. which tend to enhance antiproliferative activity and/or stimulate differentiation. A= may thus, for example, be represented by the formula (A-1)

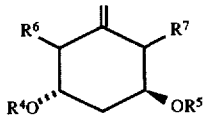
(A-1)

where $R^4$ and $R^5$, which may be the same or different, each represent a hydrogen atom or an O-protecting group, and $R^6$ and $R^7$, which may the same or different, are selected from hydrogen atoms and appropriate mono- or di-valent substituting groups.

Where $R^4$ and $R^5$ represent O-protecting groups these may, for example, be cleavable O-protecting groups such as are commonly known in the art. Suitable groups include etherifying groups such as silyl groups (e.g. tri (lower alkyl) silyl groups such as trimethylsilyl, triethylsilyl, triisopropylsilyl or t-butyldimethylsilyl; tri (aryl) silyl groups such as triphenylsilyl; and mixed alkyl-arylsilyl groups); lower (e.g. $C_{1-6}$) alkyl groups optionally interrupted by an oxygen atom, such as methyl, methoxymethyl or methoxyethoxymethyl; and cyclic groups such as tetrahydropyranyl. Esterifying O-protecting groups include lower (e.g. $C_{1-6}$) alkanoyl such as acetyl, propionyl, isobutyryl or pivaloyl; aroyl (e.g. containing 7–15 carbon atoms) such as benzoyl or 4-phenylazobenzoyl; lower alkane sulphonyl such as (optionally halogenated) methane sulphonyl; and arene sulphonyl such as p-toluene sulphonyl.

O-protected derivatives are useful as intermediates in the preparation of active 1α,3β-diols of formula (I) where $R^4$ and $R^5$ represent hydrogen atoms. Additionally, where the O-protecting groups are metabolically labile in vivo, such ethers and esters of formula (I) may be useful directly in therapy.

At least one of $R^6$ and $R^7$ is advantageously a hydrogen atom. Substituents which may be present as the other of $R^6$ and $R^7$ include, for example, methylene, methyl and spiro-linked cyclopropyl groups.

Representative A= groups falling within the above formula (A-1) include the following:

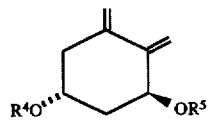
(A-2)

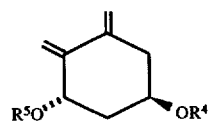
(A-3)

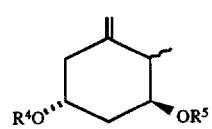
(A-4)

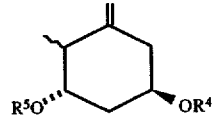
(A-5)

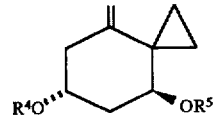
(A-6)

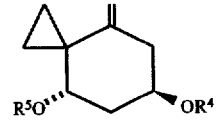
(A-7)

and

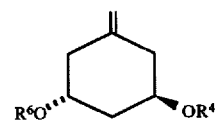
(A-8)

It will be appreciated that compounds containing groups (A-2) and (A-3) are respectively 5,6-cis (i.e. 5Z) and 5,6-trans (i.e. 5E) isomers of vitamin D analogues. Compounds containing groups (A-4) and (A-5) are similarly 5,6-cis and 5,6-trans isomers respectively of 10,19-dihydro vitamin D analogues, and compounds containing group (A-8) are 19-nor vitamin D analogues.

5,6-trans isomers according to the invention are particularly of interest as intermediates in the preparation of corresponding 5,6-cis isomers, e.g. as described in greater detail hereinafter. However, 5,6-trans isomers in which $R^4$ and $R^5$ are hydrogen atoms or metabolically labile groups will often exhibit cell modulating activity, e.g. at about one order of magnitude less than corresponding 5,6-cis isomers, and may thus be useful in therapy, especially as their effect in elevating serum calcium levels may also be reduced, thus maintaining an appreciable separation between cell modulating and calcaemic activities.

The fact that active compounds of formula (I), which may possess sizeable vitamin D-like 17-position side chains which do not carry a 24- or 25-hydroxyl group and which in many cases are not capable of being hydroxylated at these positions, exhibit cell modulating activity is unexpected in the light of previous findings in this area, which strongly suggest the necessity of such a hydroxyl group. The observation of useful cell modulating activity for active compounds of formula (I) is even more surprising in view of a report that compounds having a similar side chain but lacking a 1α-hydroxyl group are without vitamin D-like activity and are in fact useful as antagonists of vitamin D, apparently by virtue of blocking 25-hydroxylation (see U.S. Pat. No. 4,217,288).

It has also been noted (Sorensen et al., *Biochemical Pharmacology* (1990), 39, pp 391–393) that the above-mentioned 1α,24R-dihydroxy vitamin $D_3$ analogue MC-903 is oxidised in vivo to the corresponding 24-oxo compound, and that this metabolite shows considerably reduced activity as regards effects on cell proliferation and differentiation compared to MC-903. This suggests that introduction of a 24-oxo group comprises a deactivation step in respect of cell modulating activity, in contrast to our findings concerning 24-oxo and homologous compounds of the present invention.

The cell modulating activity of active compounds according to the invention, combined with their substantial lack of calcaemic effect, render them of interest (both alone and as adjuncts) in the management of neoplastic disease, particularly myelogenous leukemias. They may also be used either alone or as adjuncts in the chemotherapy of infection and in all other therapeutic modalities in which mononuclear phagocytes are involved, for example in treatment of bone disease (e.g. osteoporosis, osteopenia and osteodystrophy as in rickets or renal osteodystrophy), autoimmune diseases, host-graft reaction, transplant rejection, inflammatory diseases (including modulation of immunoinflammatory reactions), neoplasias and hyperplasias, myopathy, enteropathy and spondylitic heart disease. Active compounds according to the invention may also be useful in promoting wound healing, suppression of parathyroid hormone (e.g. as in serum calcium homeostasis) and in treatment of dermatological diseases (for example including acne, alopecia, eczema, pruritus, psoriasis and skin aging, including photoaging), hypertension, inflammation, rheumatoid arthritis, psoriatic arthritis, secondary hyperparathyroidism and asthma. The invention embraces use of these compounds in the therapy or prophylaxis of such conditions and in the manufacture of medicaments for such treatment or prophylaxis.

We believe that the active 20R isomers of formula (I) may be preferred for treatment of infections, e.g. in combination therapy, whereas the active 20S epi-isomers may be preferred for applications involving an immunosuppressive effect, e.g. in treatment of autoimmune and inflammatory diseases, rheumatoid arthritis, asthma etc. This view is supported by, for example, the work of Binderup et al. concerning 20-epi-vitamin $D_3$ analogues reported in *Biochemical Pharmacology* (1991), 42(83, pp 1569–1575.

Active compounds according to the invention may be formulated for administration by any convenient route, e.g. orally (including sublingually), parenterally, rectally, topically or by inhalation; pharmaceutical compositions so formulated comprise a feature of the invention.

Orally administrable compositions may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions may advantageously be prepared in dosage unit form. Tablets and capsules according to the invention may, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

Compositions for parenteral administration may be formulated using an injectable liquid carrier such as sterile pyrogen-free water, sterile peroxide-free ethyl oleate, dehydrated alcohol or propylene glycol or a dehydrated alcohol/propylene glycol mixture, and may be injected intravenously, intraperitoneally or intramuscularly.

Compositions for rectal administration may be formulated using a conventional suppository base such as cocoa butter or another glyceride.

Compositions for topical administration include ointments, creams, gels, lotions, shampoos, paints, powders (including spray powders), pessaries, tampons, sprays, dips, aerosols, pour-ons and drops. The active ingredient may, for example, be formulated in a hydrophilic or hydrophobic base as appropriate.

Compositions for administration by inhalation are conveniently formulated for self-propelled delivery, e.g. in metered dose form, for example as a suspension in a propellant such as a halogenated hydrocarbon filled into an aerosol container provided with a metering dispense valve.

It may be advantageous to incorporate an antioxidant, for example ascorbic acid, butylated hydroxyanisole or hydroquinone in the compositions of the invention to enhance their storage life.

Where any of the above compositions are prepared in dosage unit form these may for example contain 0.05–250 µg, e.g. 0.1–50 µg, of active compound according to the invention per unit dosage form. The compositions may if desired incorporate one or more further active ingredients.

A suitable daily dose of an active compound according to the invention may for example be in the range 0.1–500 µg, e.g. 0.2–100 µg, per day, depending on factors such as the severity of the condition being treated and the age, weight and condition of the subject.

Compounds according to the invention may be prepared by any convenient method, for example one of the following:

A) 5,6-Cis compounds of formula (I) may be prepared by isomerisation of a corresponding 5,6-trans compound, followed if necessary and/or desired by removal of any O-protecting groups. Isomerisation may be effected by, for example, treatment with iodine, with a disulphide or diselenide, or by irradiation with ultraviolet light, preferably in the presence of a triplet sensitiser.

B) 5,6-Trans compounds of formula (I) may be prepared by hydroxylating a corresponding 1-unsubstituted-5,6-trans compound, e.g. a compound (I) having an A= group of the formula

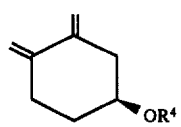

(A-9)

(where $R^4$ is hydrogen or an O-protecting group). Such hydroxylation may be effected using a selenite ester (which may be generated in situ by reaction of selenium dioxide or selenous acid and an alcohol), e.g. as described in GB-A-2038834, or using selenous acid at a pH in the range 3–9, e.g. as described in GB-A-2108506; the contents of both these specifications are incorporated herein by reference. The 1-unsubstituted-5,6-trans compound may, if desired, be prepared by isomerisation of the corresponding 5,6-cis vitamin in situ under the conditions of the oxidative reaction. The hydroxylation may, if necessary and/or desired, be followed by isomerisation and/or removal of O-protecting groups.

C) By reaction of a compound containing a precursor for the desired 17-position side chain in one or more stages and with one or more reactants serving to form the desired side chain, followed if necessary and/or desired by isomerisation and/or removal of O-protecting groups.

Such reactions can be considered as transformations of the group L in compounds of general formula (II)

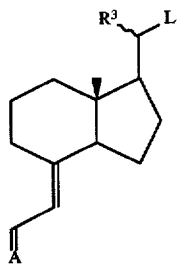

(II)

where $R^3$ and A= are as hereinbefore defined, A= preferably being one of the groups (A-2)-(A-8) in O-protected form. It should be noted that compounds (II) in which A= is as defined for (A-9) may also be employed and thereafter subjected to 1α-hydroxylation as described under (B) above.

Reactions of the compounds (II) may be divided into the following categories:

C1) Preparation of Compounds in Which Y is —$CH_2$'

Such reactions will typically involve one or more homologation stages prior to an amide formation stage, e.g. as follows:

| Step No. | Starting L | Reagent/ Reaction | Final L |
|---|---|---|---|
| 1 | —$(CH_2)_qQ$ | metal cyanide | —$(CH_2)_qCN$ |
| 2 | —$(CH_2)_qCN$ | metal hydride reducing agent capable of reducing a cyano group to an aldehyde function, preferably diisobutyl aluminium hydride* | —$(CH_2)_qCH=O$ |
| 3 | —$(CH_2)_qCH=O$ | reducing agent, e.g. $NaBH_4$, $LiAlH_4$ | —$(CH_2)_{q+1}OH$ |
| 4 | —$(CH_2)_qQ$ | metalated malonate ester | —$(CH_2)_qCH(COOR^*)_2$ |
| 5 | —$(CH_2)_q.CH(COOR^*)_2$ | i) hydrolysis to monoester ii) thermal decarboxylation | —$(CH_2)_{q+1}COOR^*$ |
| 6 | —$(CH_2)_{q+1}.COOR^*$ | reducing agent, e.g. $LiAlH_4$; Na/EtOH | —$(CH_2)_{q+2}OH$ |
| 7 | —$(CH_2)_qQ$ | metalated acetamide derivative | —$(CH_2)_{q+1}.CO.NR^1R^2$ |
| 8 | —$(CH_2)_q.COOR^*$ | amine or aminating agent from same (directly or indirectly) | —$(CH_2)_qCONR^1R^2$ |

*see Ando et al., Chem. Pharm. Bull.(1992), 40, p 1662
Key
$R^1$ and $R^2$ are as defined above;
q is zero or an integer;
Q is a leaving group, e.g. a sulphonate ester group such as lower alkyl sulphonyloxy, lower fluoroalkyl sulphonyloxy or aryl sulphonyloxy or, more preferably, a halogen atom such as chlorine, bromine or iodine; and
$R^*$ is an esterifying group, e.g. a hydrocarbyl group such as a lower alkyl or aryl group.

It will be appreciated that the hydroxyl groups in the products of steps 3 and 6 may be converted to leaving groups Q, e.g. by reactions such as tosylation, whereafter the products may be subjected to further homologation sequences, e.g. according to steps 1–3 or steps 4–6, and/or to amide formation, e.g. according to step 7.

Step 8 may be effected indirectly by, for example, hydrolysis of the ester to the corresponding acid in which L is the group —$(CH_2)_q$COOH and reacting this with the amine $R^1R^2$NH, e.g. in the presence of a coupling agent such as dicyclohexylcarbodiimide; alternatively the acid may be converted to a reactive derivative such as an acyl halide and thereafter reacted with the amine $R^1R^2$NH. Direct amide formation may be effected by reaction of the ester with the amine $R^1R^2$NH but is more preferably performed using an activated metalated derivative of the amine, e.g. tin (II) amides as described by Wang et al. (J.Org.Chem. (1992), 57, pp 6101–6103).

Useful starting materials for the above sequences of reactions include compounds of formula (III)

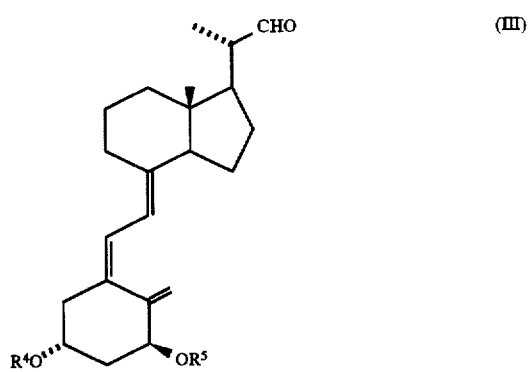

(III)

(where $R^4$ and $R^5$ are as defined above) and/or 5,6-trans isomers thereof and the corresponding 1-deoxy compounds; such compounds may be obtained through oxidative cleavage (e.g. by ozonolysis) of the 22,23-double bond of vitamin $D_2$, 1α-hydroxy vitamin $D_2$ or O-protected derivatives thereof, these preferably being stabilised by formation of a Diels Alder dienophile adduct, e.g. with sulphur dioxide or a diazacyclo compound, for example as described in GB-A-2114570 (the contents of which are incorporated herein by reference).

Such 20S compounds (III), preferably still in the form of their dienophile adducts, may be isomerised by, for example, treatment with a mild base, e.g. an inorganic base such as sodium bicarbonate or a tertiary organic base such as 1,4-diazabicyclo [2.2.2]octane ("DABCO") or 1,8-diazabicyclo [5.4.0]undec-7-ene ("DBU"). This yields a mixture of 20R and 20S isomers from which the pure 20R epi-isomer may be isolated chromatographically; alternatively separation of a desired epi-isomer may be delayed until a later stage in the synthesis, up to and including the final step.

Reduction of the aldehyde grouping of a compound (III) or a corresponding epi-isomer, e.g. using a metal hydride reducing agent such as sodium borohydride, yields a corresponding hydroxymethyl compound, i.e. a compound (II) in which L is —$CH_2OH$. This may be converted to a compound (II) in which L is —$CH_2Q$ as defined above by, for example, conversion to a sulphonate ester (e.g. to a tosylate) followed, if desired, by nucleophilic displacement of the sulphonate group by reaction with a halide salt (e.g. an alkali metal bromide).

Compounds (III) may also be oxidatively decarbonylated, e.g. as described in WO90/09991 using oxygen with cupric acetate, 2,2'-bipyridyl and DABCO as catalyst, to yield the corresponding 20-keto compound.

This may be reduced to yield a 20-hydroxy compound which may in turn be converted to a compound (II) where L is a group —(CH$_2$)$_q$Q in which q=0, e.g. by tosylation. The nature of the reducing agent with which the 20-ketone is reacted may influence the stereochemistry of the product; thus, for example, sodium borohydride tends to lead to a 20-hydroxy compound in which the 21-methyl group is in the β-configuration, whereas lithium aluminium hydride or sodium in ethanol favour formation of products where the 21-methyl group is in the α-configuration.

It will be appreciated that any subsequent reactions involving nucleophilic displacement of the 20-hydroxy group or a leaving group derived therefrom will promote inversion of the configuration about the C$_{20}$ carbon atom. It will therefore be necessary to start from a configuration opposite to that ultimately desired where the reaction sequence involves an odd number of such nucleophilic displacements at C$_{20}$.

Compounds of formula (II) in which A= represents a group (A-9) as hereinbefore defined and L represents an O-protected hydroxyl or hydroxymethyl group (e.g. in which the hydroxyl group is esterified, for example with a lower alkanoyl group such as acetyl) may be subjected to 1α-hydroxylation as described under (B) above to give compounds (II) in which A= represents a group (A-2) or (A-3) as hereinbefore defined in which R$^5$ represents hydrogen. Such compounds or protected derivatives thereof, e.g. in which R$^5$ is trimethylsilyl, may be hydrogenated (e.g. in the presence of a noble metal catalyst such as tris-triphenylphosphine rhodium chloride) to yield corresponding compounds in which A= represents a group (A-4) or (A-5) as hereinbefore defined, or may be cyclopropanated (e.g. by reaction with methylene iodide in the presence of zinc/copper couple) to yield corresponding compounds in which A= represents a group (A-6) or (A-7) as hereinbefore defined. Where appropriate, the compounds so obtained may be converted to compounds in which R$^5$ is an O-protecting group (e.g. by silylation) and may be hydrolysed (e.g. with base such as potassium hydroxide or potassium carbonate) or reduced (e.g. with lithium aluminium hydride) to remove the side chain ester group to yield useful starting materials (II) in which L represents —OH or —CH$_2$OH.

Compounds of formula (II) in which A= represents a group (A-8) as hereinbefore defined and L is —CH$_2$OH or —CHO may be prepared as described by Perlman et al., *Tetrahedron Letters* (1992), 33, pp 2937–2940.

C2) Preparation of Compounds in Which Y is —O—

This may conveniently be effected by reaction of a compound (II) in which L is a group —X.OH (where X is as defined for formula (I)), e.g. prepared as described in (C1) above, with a compound of formula (IV)

Q.Z.CO.NR$^1$R$^2$ (IV)

(where R$^1$,R$^2$ and Z are as defined for formula (I) and Q is as hereinbefore defined, preferably a halogen atom), or when Z is a valence bond and R$^1$ is a hydrogen atom, with a compound of formula (IVa)

O=C=NR$^2$ (IVa)

Alternativewly the amide derivative may be formed indirectly, e.g. by reaction firstly with a compound of formula (V)

Q.Z.CO.OR$^e$ (V)

(where Q, Z and R$^e$ are as hereinbefore defined, the esterifying group R$^e$ being, for example a branched or unbranched aliphatic group, e.g. a tertiary alkyl group such as t-butyl, or an aromatic group, e.g. a 2,6-dialkylphenyl or 2,4,6-trialkylphenyl group such as 2,4-xylyl or mesityl). The resulting ester may be converted to the desired amide e.g. as described for step 8 in (C1) above.

It will be appreciated that it may equally well be possible to employ starting materials of formula (II) in which L is a group —X.Q (the symbols having the above-defined meanings and Q preferably being a highly reactive leaving group such as trifluoroacetate, tosylate or trifluoromethanesulphonate) and react these with compounds of formulae (VI) or (VII)

HO.Z.CO.NR$^1$R$^2$ (VI)

HO.Z.CO.OR$^e$ (VII)

(where R$^1$,R$^2$,R$^e$ and Z are as hereinbefore defined).

A further method useful in the preparation of compounds (I) in which Z is an ethylene group comprises the base catalysed Michael addition of a compound (II) in which L is —X.OH (where X is as hereinbefore defined) to an acrylate ester, e.g. of formula (VIII)

CH$_2$=CH.CO.OR$^e$ (VIII)

(where R$^e$ is as hereinbefore defined), followed by conversion of the ester grouping to the desired amide, e.g. as described for step 8 in (C1) above.

Reagents such as the compounds of formula (IV) above may be prepared by, for example, reaction of an appropriate ω-haloalkanoyl chloride (e.g. 4-bromobutyryl chloride where it is desired to synthesise a compound (I) in which Z is a trimethylene grop) with an amine R$^1$R$^2$NH (where R$^1$ and R$^2$ are as hereinbefore defined). It is convenient to prepare such a reagent in situ, i.e. without subsequent purification, preferably using a molar excess of the amine so as to leave a sufficient excess of base to react with acid liberated in the ensuing coupling with a compound (II) in which L is —X.OH (where X is as hereinbefore defined).

C3) Preparation of Compounds in Which Y is —S—

This may, for example, be effected by reaction of a compound (II) in which L represents —X.Q (the symbols having the above-defined meanings) with an ω-mercaptoamide of formula (IX)

HS.Z.CO.NR$^1$R$^2$ (IX)

(wherein R$^1$,R$^2$ and Z are as hereinbefore defined, or by the converse reaction of a compound (II) wherein L is —X.SH (X being as hereinbefore defined) with a compound of formula (IV) or formula (IVa) above, the reaction in each case being effected in the presence of base.

Alternatively, the compounds (II) may first be converted to ester derivatives, followed by conversion of the ester grouping to the desired amide, e.g. as described for step 8 in (C1) above.

Starting materials of formula (II) in which L is a group —X.SH (X being as hereinbefore defined) may, for example, be prepared from a corresponding compound in which L is —X.Q (X and Q being as hereinbefore defined), e.g. by reaction with a thiolic acid or a xanthate salt, followed by generation of the required thiol group, e.g. by reaction with ammonia.

C4) Preparation of Compounds in Which Y is —NR—

One appropriate reaction comprises reductive amination using an appropriate 20-ketone or a compound (II) in which L is —X'.CHO (where X' is a valence bond or a methylene group) and a compound of formula (X)

$$HNR.Z.CO.NR^1R^2 \quad (X)$$

(where R, R$^1$, R$^2$ and Z are as hereinbefore defined). Reaction starting from the 20-ketone will predominantly yield epi-isomers.

Alternatively, a compound (II) in which L represents a group —X.NHR (where X and R are as hereinbefore defined), or more preferably an activated group —X.N=P (R$^P$)$_3$ obtained by reaction of an azide where L is —X.N$_3$ with a phosphine P(R$^P$)$_3$ (where X is as hereinbefore defined and R$^P$ represents a hydrocarbyl group), may be alkylated/ acylated by reaction with a compound of formula (IV) of formula (IVa) above.

The converse reaction of a compound (II) in which L represents —X.Q (the symbols being as hereinbefore defined and Q preferably being a highly reactive leaving group such as trifluoroacetate, tosylate or trifluoromethanesulphonate) with a compound of formula (X) above may likewise be employed, the amine (X) preferably being used in large excess.

Again it may be preferred in any of the above procedures initially to introduce a terminal ester group and thereafter convert this to the desired amide grouping, e.g. as described for step 8 in (C1) above.

D) By reaction of a compound of formula (I) to modify the substitution pattern about the A= group, followed if necessary and/or desired by isomerisation and/or removal of protecting groups.

Thus for example, compounds (I) in which A= represents a group (A-4) or (A-5) may be prepared by hydrogenation of corresponding compounds in which A= represents (A-2) or (A-3), e.g. using the method of GB-A-1583749. It will be appreciated that such hydrogenation may alternatively be effected at an earlier stage of a reaction sequence, e.g. on a starting material or intermediate of formula (II).

Compounds (I) in which A= represents a group (A-6) or (A-7) may be prepared from corresponding compounds in which A= represents (A-2) or (A-3) (in which R$^4$ is an O-protecting group and R$^5$ is a hydrogen atom or a trimethylsilyl group) by Simmons-Smith methylenation (see e.g. Neef et al., *Tetrahedron Letters* (1991), 32, pp 5073–5076).

Compounds (I) in which A= represents a group (A-8) may, for example, be prepared by cleavage of the 7,8-double bond of an appropriate vitamin D derivative (e.g. a precursor compound (I) in which A= is a group (A-9)), for example by ozonolysis or by successive reaction with potassium permanganate and sodium periodate, followed by Wittig-Horner reaction of the resulting 8-one with an appropriate ring A precursor, e.g. of formula (XI)

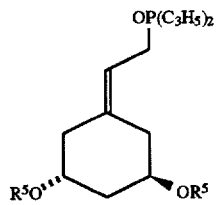

(where R$^4$ and R$^5$ represent O-protecting groups)—see, for example, Perlman et al., *Tetrahedron Letters* (1992), 33, pp 2937–2940.

In general, either 5,6-cis or 5,6-trans geometry may be present at any of the various steps described in (C) and (D) above, although it may be preferred to employ 5,6-trans isomers in the above-mentioned 1α-hydroxylation and 22,23-double bond oxidative cleavage reactions. Conversion of 5,6-trans geometry to 5,6-cis is thus most advantageously effected after introduction of the 1α-hydroxyl group.

It will be appreciated that many of the reaction sequences described above may also be accomplished using appropriate steroid-5,7-dienes (or steroid-5-enes which are convertible into such dienes), followed by conversion of the steroid products into the desired vitamin D analogues, e.g. by irradiation with UV light.

In general, O-protecting groups present at the 1α- and/or 3β-positions may be removed by, for example, conventional methods such as are well documented in the literature. Thus esterifying acyl groups may be removed by basic hydrolysis, e.g. using an alkali metal alkoxide in an alkanol. Etherifying groups such as silyl groups may be removed by acid hydrolysis or treatment with a fluoride salt, e.g. a tetraalkyl ammonium fluoride. The use of such acid-labile but base-stable protecting groups may be of advantage when reacting compounds of formula (II), in view of the strongly basic conditions normally employed in the homologation steps used to build up the desired side chain.

The following non-limitative examples serve to illustrate the invention. All temperatures are in °C.

PREPARATION 1 a) 20α-Acetoxymethyl-1α-hydroxy-3β-triisopropylsilyloxy-9,10-secopregna-5(E),7-diene [Formula (II)—A=(A-5), R$^3$=α-CH$_3$, R$^4$=(i-Pr)$_3$ Si, R$^5$=H, L=CH$_2$.O.CO.CH$_3$]

A solution of tris-triphenylphosphine rhodium chloride (450 mg) in benzene (30 ml) (or in a 1:1 mixture of benzene and ethanol) is stirred under hydrogen until no further uptake is observed. A solution of 20α-acetoxymethyl-1α-hydroxy-3β-triisopropylsilyloxy-9,10-secopregna-5(E),7,10(19)-triene [Formula (II)—A=(A-3), R$^3$=α-CH$_3$, R$^4$=(i-Pr)$_3$ Si, R$^5$=H, L=CH$_2$.O.CO.CH$_3$,—as an alternative the corresponding 1α-trimethylsilyl ether may be used] (500 mg) in benzene (30 ml) is added and the mixture stirred under hydrogen until 1 equivalent of hydrogen has been taken up (ca 21 ml). The title compounds are purified by chromatography [the 10(R) and 10(S) isomers may optionally be resolved at this stage] and have UV λ$_{max}$ ca. 243,251 and 261 nm, with ε=ca 35,000; 40,000 and 27,000 respectively.

b) 1α,3β-Bis-triisopropylsilyloxy-20α-hydroxymethyl-9,10-secopregna-5(E),7-diene [Formula (II)—A=(A-5), R$^3$=α-CH$_3$, R$^4$=R$^5$=(i-Pr)$_3$ Si, L=CH$_2$OH]

The diene from (a) above (ca 500 mg) in dichloromethane (2 ml) is treated with chlorotriisopropylsilane (250 mg) and imidazole (350 mg) and the mixture stirred overnight at room temperature. After work up the crude bis-silyl ether is dissolved in tetrahydrofuran (10 ml), treated with lithium aluminium hydride (100 mg) and stirred at room temperature for 1–2 hours. After decomposition of the excess lithium aluminium hydride (careful addition of saturated aqueous sodium sulphate) the reaction mixture is worked up to afford the title alcohol.

PREPARATION 2

1α,3β-Bis-triisopropylsilyloxy-20α-hydroxymethyl-9,10-secopregna-5(Z),7-diene [Formula (II)—A=(A-4), R$^3$=α-CH$_3$, R$^4$=R$^5$=(i-Pr)$_3$ Si, L=CH$_2$OH]

The 5(E)-triene starting material in Preparation 1(a) is photoisomerised in benzene in the presence of phenazine by irradiation for 1 hour, to yield the corresponding 5(Z)-triene. This product is hydrogenated as described in Preparation l(a) and silylated and de-acetylated as described in Preparation l(b) to give the title compound. UV $\lambda_{max}$ ca. 243, 251 and 261 nm with $\epsilon$=ca. 35,000; 40,000 and 27,000 respectively.

The epi (i.e. 20β-hydroxymethyl) compounds corresponding to the products of Preparations 1 and 2 are prepared by the same procedures starting with the 20-epi compound 20β-acetoxymethyl-1α-hydroxy-3β-triisopropylsilyloxy-9,10-secopregna-5(E),7,10(19)-triene [Formula (II)—A (A-3), $R^3$=β-$CH_3$, $R^4$=(i-Pr)$_3$ Si, $R^5$=H, L=$CH_2.O.CO.CH_3$]. This is itself prepared by isomerisation of the 20-aldehyde obtained by ozonolysis of the sulphur dioxide adduct of vitamin $D_2$ followed by reduction and 1α-hydroxylation of the 20-epi aldehyde.

PREPARATION 3 a) 20α-Acetoxymethyl-1α-hydroxy-3β-triisopropylsilyloxy-10-spirocyclopropyl-9,10-secopregna-5(E),7-diene [Formula (II)—A=(A-7), $R^3$=α-$CH_3$, $R^4$=(i-Pr)$_3$ Si, $R^5$=H, L=$CH_2.O.CO.CH_3$]

A mixture of zinc/copper couple (1.08 g) and diiodomethane (0.9 ml) in ether (6 ml) is heated under reflux with stirring for 40 minutes. A solution of 20α-acetoxymethyl-1α-hydroxy-3β-triisopropylsilyloxy-9,10-secopregna- 5(E),7,10(19)-triene [Formula (II)—A=(A-3), $R^3$=α-$CH_3$, $R^4$=(i-Pr)$_3$ Si, $R^5$=H, L=$CH_2.O.CO.CH_3$—as an alternative the corresponding 1α-trimethylsilyl ether may be used) (ca 500 mg) in ether (9 ml) is added, and the mixture is stirred and heated under reflux until most of the starting material has disappeared (TLC control: usually about 4 hours for the 1α-trimethylsilyl ether, less for the 1α-hydroxy compound). The reaction mixture is filtered, the solvent removed and the product chromatographed to remove the remaining diiodomethane. The title compound has UV $\lambda_{max}$ ca. 246, 253 and 263 nm, with $\epsilon$=ca. 29,000; 36,000 and 25,000 respectively.

b) 1α,3β-Bis-triisopropylsilyloxy-20α-hydroxymethyl-10-spirocyclopropyl-9,10-secopregna-5(E),7-diene [Formula (II)—A=(A-7), $R^3$=α-$CH_3$, $R^4$=$R^5$=(i-Pr)$_3$ Si, L=$CH_2OH$]

The diene from (a) above (ca 500 mg) in dichloromethane (2 ml) is treated with chlorotriisopropylsilane (250 mg) and imidazole (350 mg) and the mixture stirred overnight at room temperature. After work up the crude bis-silyl ether is dissolved in tetrahydrofuran (10 ml), treated with lithium aluminium hydride (100 mg) and stirred at room temperature for 1–2 hours. After decomposition of the excess lithium aluminium hydride (careful addition of saturated aqueous sodium sulphate) the reaction mixture is worked up to afford the title alcohol.

PREPARATION 4

1α,3β-Bis-triisopropylsilyloxy-20α-hydroxymethyl-10-spirocyclopropyl-9,10-secopregna-5(Z) 7-diene [Formula (II)—A=(A-6), $R^3$=α-$CH_3$, $R^4$=$R^5$=(i-Pr)$_3$ Si, L=$CH_2OH$]

The procedure of Preparation 3(a) is repeated starting from the corresponding 5(Z)-triene, prepared by photoisomerization of the 5(E)-triene as described in Preparation 2; the reaction of the 5(Z)-triene is somewhat slower than that of the 5(E)-triene. Silylation and de-acetylation as described in Preparation 3(b) gives the title compound. UV $\lambda_{max}$ ca. 246, 253 and 263 nm with $\epsilon$=ca. 29,000; 36,000 and 25,000 respectively.

EXAMPLE 1 a) 1α,3β-Bis-triisopropylsilyloxy-20-epi-22-oxa-9,10-secochola-5(E),7,10(19)-trienic Acid, Piperidine Amide, [Formula (I)—A=(A-3), $R^1$+$R^2$=—($CH_2$)$_5$—, $R^3$=β-$CH_3$, $R^4$=$R^5$=(i-Pr)$_3$ Si, X=valence bond, Y=O, Z=$CH_2$]

A solution of 18-crown-6-ether (132 mg) in tetrahydrofuran (2 ml) was added dropwise to a solution of 1α,3β-bis-triisopropylsilyloxy-20β-hydroxy-9,10-secopregna-5(E),7,10-(19)-triene [Formula (II)—A=(A-3), $R^3$=β-$CH_3$, $R^4$=$R^5$=(i-Pr)$_3$ Si, L=OH] (194 mg) and potassium hydride (0.15 ml of a 35 wt % dispersion in mineral oil) in tetrahydrofuran (1 ml). The resulting mixture was cooled to −10° and treated with a solution of N-(bromoacetyl)piperidine (315 mg) in tetrahydrofuran (1 ml) added dropwise. After 15 minutes the reaction mixture was brought to room temperature, stirred for 4 hours, then treated with ammonium chloride and worked up. The crude product was chromatographed to give first the starting alcohol (80 mg) and then the title product (80 mg). UV ($Et_2O$) $\lambda_{max}$ 268, $\lambda_{min}$ 235 nm; IR ($CCl_4$) $v_{max}$ 1640, 1460 cm$^{-1}$; NMR ($CCl_4$) δ 5.4–6.4 (2H, ABq, 6,7-H's), 4.7–4.9 (2H, bs, 19-H's), 4.0–4.7 (2H, bm, 1,3-H's), 3.83 (2H, s, O—$CH_2$C=O), 3.1–3.6 (4H, bm, N$CH_2$), 0.57 (3H, s, 18-H's).

b) 1α,3β-Bis-triisopropylsilyloxy-20-epi-22-oxa-9,10-secochola-5(Z),7,10(19)-trienic Acid, Piperidine Amide, [Formula (I)—A=(A-2), $R^1$+$R^2$=—($CH_2$)$_5$—, $R^3$=β-$CH_3$, $R^4$=$R^5$=(i-Pr)$_3$ Si, X=valence bond, Y=O, Z=$CH_2$]

A solution of the 5(E) product from (a) above (80 mg) and phenazine (36 mg) in benzene (10 ml) was irradiated for 1 hour. The solvent was then removed and the title 5(Z) product isolated by chromatography (65.2 mg). NMR ($CCl_4$) δ 5.6–6.2 (2H, ABq, 6,7-H's), 4.6 and 5.2 (1H ea, s, 19-H's), 4.0–4.6 (2H, bm, 1,3-H's), 3.77 (2H, s, O—$CH_2$C=O), 3.1–3.6 (4H, bm, N$CH_2$), 0.53 (3H, s, 18-H's).

c) 1α,3β-Dihydroxy-20-epi-22-oxa-9,10-secochola-5(Z),7,10(19)-trienic Acid, Piperidine Amide, [Formula (I)—A=(A-2), $R^1$+$R^2$=—($CH_2$)$_5$—, $R^3$=β-$CH_3$, $R^4$=$R^5$=(H), X=valence bond, Y=O, Z=$CH_2$]

The bis-silyl ether from (b) above (62.5 mg) in tetrahydrofuran (1 ml) was treated with tetrabutylammonium fluoride (1 ml of a 1M solution in tetrahydrofuran). After 4 hours the reaction mixture was worked up and the desilyated title product isolated by preparative TLC (30% methanol in ethyl acetate) (30.4 mg). UV (EtOH) $\lambda_{max}$ 263, $\lambda_{min}$ 228 nm; IR ($CDCl_3$) $v_{max}$ 3160–3640, 1630, 1450 cm$^{-1}$; NMR ($CCl_4$) δ 5.7–6.6 (2H, ABq, 6,7-H's), 4.8 and 5.3 (1H ea, s, 19-H's), 3.9–4.5 (4H, bm, 1,3-H's and O—$CH_2$C=O), 3.1–3.7 (4H, bm, N$CH_2$), 1.1 (2H, d, j=5 hz, 21-H's), 0.57 (3H, s, 18-H's).

EXAMPLE 2 a) 1α,3β-Bis-triisopropylsilyloxy-20-epi-23-homo-22-oxa-9,10-secochola-5(E),7,10(19)-trienic Acid, Piperidine Amide, [Formula (I)—A=(A-3), $R^1$+$R^2$= —($CH_2$)$_5$—, $R^3$=β-$CH_3$, $R^4$=$R^5$=(i-Pr)$_3$ Si, X= valence bond, Y=O, Z=($CH_2$)$_2$]

1α,3β-bis-triisopropylsilyloxy-20β-hydroxy-9,10-secopregna-5(E),7,10(19)-triene [Formula (II)—A=(A-3), $R^3$=O—$CH_3$, $R^4$=$R^5$=(i-Pr)$_3$ Si, L=OH] (539 mg) was vigorously stirred with ethyl acrylate (2.1 ml) under phase transfer conditions [toluene (21 ml), 50% aqueous sodium hydroxide (9 ml) and tetrabutylammonium hydroxide (0.135 ml of 10% w/w in water) for 2 hours at room temperature]. The aqueous phase was removed and replaced with fresh portions of ethyl acrylate, sodium hydroxide and quaternary ammonium hydroxide and stirring continued for 2 hours. The latter process was repeated 3 more times, then the organic layer was removed and worked up. Chromatography of the crude product afforded the ethyl ester corresponding to the title amide (160 mg) and then the starting alcohol (178 mg). The ester had UV (Et$_2$O) $\lambda_{max}$ 269, $\lambda_{min}$ 228 nm; IR (CCl$_4$) $\nu_{max}$ 1630 cm$^{-1}$; NMR (CCl$_4$) δ 5.2–6.3 (2H, ABq, 6,7-H's), 4.6–4.9 (2H, bs, 19-H's), 4.2–4.6 (2H, bm, 1,3-H's), 3.6–4.2 (2H, q, O—$CH_2CH_3$), 2.9–3.6 (m, O—C$\underline{H}_2CH_2C$=O), 0.57 (3H, s, 18-H's).

The ester (106 mg) in hexane (1 ml) was treated at -78° with the reagent (2 ml) prepared by treating Sn[N(TMS)$_2$]$_2$ (4 ml of 0.1M solution in hexane) with piperidine (34 mg). The reaction mixture was brought to room temperature and as TLC showed that starting ester remained the reaction mix was treated as above with the remainder of the tin reagent. The reaction was worked up (including treatment with methanol and potassium fluoride to remove tin) and the crude product chromatographed to give starting ester (12 mg) and the title amide (42 mg). UV (Et$_2$O) $\lambda_{max}$ 269, $\lambda_{min}$ 229 nm; IR (CCl$_4$) $\nu_{max}$ 1640, 1460 cm$^{-1}$; NMR (CCl$_4$) δ 5.3–6.5 (2H, ABq, 6,7-H's), 4.6–5.07 (2H, bs, 19-H's), 3.8–4.7(bm, 1,3-H's), 2.7–3.5 (bm, NC$\underline{H}_2$), 0.53 (3H, s, 18-H's).

b) 1α,3β-Bis-triisopropylsilyloxy-20-epi-23-homo-22-oxa-9,10-secochola-5(Z),7,10(19)-trienic Acid, Piperidine Amide [Formula (I)—A=(A-2), R$^1$+R$^2$—(CH$_2$)$_5$—, R$^3$=β-CH$_3$, R$^4$=R$^5$=(i-Pr)$_3$Si, X=valence bond, Y=O, Z=(CH$_2$)$_2$]

The 5(E)-amide from (a) above (67 mg) sensitized by phenazine (29 mg) was photoisomerised as per Example 1(b) and the product isolated by chromatography to afford the 5(Z) title compound (54.9 mg). UV (Et$_2$O) $\lambda_{max}$ 262, $\lambda_{min}$ 227 nm; IR (CCl$_4$) $\nu_{max}$ 1640, 1460 cm$^{-1}$; NMR (CCl$_4$) δ 5.6–6.3 (2H, ABq, 6,7-H's), 4.5 and 5.2 (1H ea, bs, 19-H's), 3.9–4.5 (bm, 1,3-H's), 3.0–3.7 (bm, NC$\underline{H}_2$), 0.50 (3H, s, 18-H's).

c) 1α,3β-Dihydroxy-20-epi-23-homo-22-oxa-9 10-secochola-5(Z),7,10(19)-trienic Acid, Piperidine Amide [Formula (I)—A=(A-2), R$^1$+R$^2$=—(CH$_2$)$_5$, R$^3$=β-CH$_3$, R$^4$=R$^5$=H, X=valence bond, Y=O, Z=(CH$_2$)$_2$]

The silylated compound from (b) above (54 mg) was desilylated as in Example 1(c) to give the title diol (28 mg). UV (EtOH) $\lambda_{max}$ 263, $\lambda_{min}$ 227 nm; IR (CDCl$_3$) $\nu_{max}$ 3200–3660, 1640, 1460 cm$^{-1}$; NMR (CDCl$_3$) δ 5.6–6.5 (2H, ABq, 6,7-H's), 4.7 and 5.4 (1H ea, bs, 19-H's), 3.6–4.6 (bm, 1,3-H's, 3.1–3.6 (bm, NC$\underline{H}_2$), 2.3–2.9 (2H, t, CH$_2$C$\underline{H}_2$—C=O), 1.05 (3H, d, j=6Hz, 21-H's), 0.53 (3H, s, 18-H's)

The corresponding dimethylamine and cyclopropylamine amide analogues (R$^1$=R$^2$=CH$_3$ and R$^1$=H, R$^2$=cyclopropyl respectively) are prepared using dimethylamine or cyclopropylamine in place of piperidine in (a) above and thereafter proceeding as in (b) and (c).

EXAMPLE 3 a) 1α,3β-Bis-triisopropylsilyloxy-20-epi-22-oxa-9,10-secochola-5(E),7,10(19)-trienic Acid, Morpholine Amide [Formula (I)—A=(A-3), R$^1$+R$^2$=—(CH$_2$)$_2$—O—(CH$_2$)$_2$—, R$_3$=β-CH$_3$, R$^4$=R$^5$=(i-Pr)$_3$Si, X=valence bond, Y=O, Z=CH$_2$]

A solution of 18-crown-6-ether (264 mg) in tetrahydrofuran (4 ml) was added dropwise to a solution of 1α,3β-bis-triisopropylsilyloxy-20β-hydroxy-9,10-secopregna-5(E),7,10(19)-triene [Formula (II)—A=(A-3), R$^3$=β-CH$_3$, R$^4$=R$^5$=(i-Pr)$_3$ Si, L=OH] (306 mg) and potassium hydride (0.9 ml of a 11.7 wt. % dispersion in mineral oil) in tetrahydrofuran (2 ml). The resulting mixture was cooled to −10° and treated with a solution of N-(bromoacetyl) morpholine (686 mg) in tetrahydrofuran (3 ml) added dropwise. After 15 minutes the reaction mixture was brought to room temperature, stirred for 2 hours, then treated with ammonium chloride and worked up. The crude product was chromatographed to give first the starting alcohol (80 mg) and then the title product (80.2 mg). UV (Et$_2$O) $\lambda_{max}$ 269, $\lambda_{min}$ 231 nm; IR (CCl$_4$) $\nu_{max}$ 1650, 1460 cm$^{-1}$; NMR (CCl$_4$) δ 5.3–6.3 (2H, ABq, 6,7-H's), 4.7–5 (2H, bs, 19-H's), 4.0–4.7 (bm, 1,3,20-H's), 3.87 (2H, s, O—C$\underline{H}_2$C=O), 3.1–3.7 (mostly 3.47) (8H, m, morpholine-H's), 0.67 (3H, s, 18-H's).

b) 1α,3β-Bis-triisopropylsilyloxy-20-epi-22-oxa-9,10-secochola-5(Z),7,10(19)-trienic Acid, Morpholine Amide [Formula (I)—A=(A-2), R$^1$+R$^2$=—(CH$_2$)$_2$—O—(CH$_2$)$_2$—, R$^3$=β-CH$_3$, R$^4$=R$^5$=(i-Pr)$_3$Si, X=valence bond, Y=O, Z=CH$_2$]

A solution of the 5(E) product from (a) above (109 mg) and phenazine (506 mg) in benzene (14 ml) was irradiated for 1 hour. The solvent was then removed and the title 5(Z)—product isolated by chromatography (87 mg). UV (Et$_2$O) $\lambda_{max}$ 261, $\lambda_{min}$ 228 nm; IR (CCl$_4$) $\nu_{max}$ 1645, 1455 cm$^{-1}$; NMR (CCl$_4$) δ 5.5–6.3 (2H, ABq, 6,7-H's), 4.6 and 5.2 (1H ea, s, 19-H's), 4.0–4.6 (bm, 1,3,20-H's), 3.87 (2H, s, O—C$\underline{H}_2$C=O), 3.1–3.6 (8H, m, morpholine-H's), 0.53 (3H, s, 18-H's).

c) 1α,3β-Dihydroxy-20-epi-22-oxa-9,10-secochola-5(Z),7,10(19)-trienic Acid, Morpholine Amide [Formula (I)—A=(A-2), R$^1$+R$^2$=—(CH$_2$)$_2$—O—(CH$_2$)$_2$—, R$^3$=β-CH$_3$; R$^4$=R$^5$=H, X=valence bond, Y=O, Z=CH$_2$]

The bis-silyl ether from (b) above (87 mg) in tetrahydrofuran (1 ml) was treated with tetrabutylammonium fluoride (0.68 ml of a 1M solution in tetrahydrofuran). After 3 hours the reaction mixture was worked up and the desilylated title product isolated by preparative TLC (7% methanol in ethyl acetate) (40.9 mg). UV (EtOH) $\lambda_{max}$ 263, $\lambda_{min}$ 228 nm; IR (CDCl$_3$) $\nu_{max}$ 3160–3630, 1635, 1450 cm$^{-1}$; NMR (CDCl$_3$) δ 5.5–6.5 (2H, ABq, 6,7-H's), 4.7 and 5.3 (1H ea, s, 19-H's), 3.8–4.5 (bm, 1,3,20-H's), 3.98 (d, O—C$\underline{H}_2$C=O), 3.1–3.8 (8H, m, morpholine-H's), 1.08 (2H, d, j=5Hz, 21-H's), 0.57 (3H, s, 18-H's).

EXAMPLE 4 a) 1α,3β-Bis-triisopropylsilyloxy-20-epi-23-bis-homo-22-oxa-9,10-secochola-5(E),7,10(19)-trienic Acid, Piperidine Amide [Formula (I)—A=(A-3), R$^1$+R$^2$=—(CH$_2$)$_5$—, R$^3$=β-CH$_3$, R$^4$=R$^5$=(i-Pr)$_3$Si, X=valence bond, Y=O, Z=(CH$_2$)$_3$]

A solution of 4-bromobutyryl chloride (6.2 g) in ether (30 ml) was added dropwise at 0° to piperidine (5.8 g) in ether (150 ml). The reation mixture was stirred for 0.5 hour at 0° followed by 2 hours at room temperature. The ether solution was washed successively with water, saturated aqueous sodium bicarbonate and brine, then dried and concentrated in vacuo to give 3.33 g of a solid product which had IR (CDCl$_3$) $\nu_{max}$ 1690, 1630 cm$^{-1}$. The reagent thus prepared was used as set out below without further processing.

A solution of 18-crown-6-ether (198 mg) in tetrahydrofuran (4 ml) was added dropwise to a mixture of 1α,3β-bis-triisopropylsilyloxy-20β-hydroxy-9,10-secopregna-5(E),7,10(19)-triene [Formula (II)—A=(A-3), R$^3$=β-CH$_3$, R$^4$=R$^5$=(i-Pr)$_3$Si, L=OH] (255 mg) and potassium hydride (0.225 ml of a 35 wt. % dispersion in mineral oil) in tetrahydrofuran (1 ml). The resulting mixture was cooled to 0° and treated with 526 mg of the reagent prepared as described above. After 15 minutes the reaction mix was brought to room temperature, stirred overnight, then treated with ammonium chloride and worked up. The crude product was chromatographed to give the title product (53 mg). UV (Et$_2$O) ν$_{max}$ 270, λ$_{min}$ 232 nm; IR (CCl$_4$) ν$_{max}$ 1615, 1445 cm$^{-1}$; NMR (CCl$_4$) δ 5.2–6.4 (2H, ABq, 6,7-H's), 4.5–4.9 (2H, bs, 19-H's), 3.7–4.5 (bm, 1,3,20-H's), 3.1–3.7 (bm, NC$\underline{H}_2$, OC$\underline{H}_2$), 0.6 (3H, s, 18-H's).

b) 1α,3β-Bis-triisopropylsilyloxy-20-epi-23-bis-homo-22-oxa-9,10-secochola-5(Z) 7,10(19)-trienic Acid, Piperidine Amide [Formula (I)—A=(A-2), R$^1$+R$^2$=—CH$_2$—, R$^3$=β-CH$_3$, R$^4$=R$^5$=(i-Pr)$_3$Si, X=valence bond, Y=O, Z=(CH$_2$)$_3$]

A solution of the 5(E) product from (a) above (53 mg) and phenazine (25 mg) in benzene (7 ml) was irradiated for 1 hour. The solvent was then removed and the title 5(Z) product isolated by chromatography (30 mg). UV (Et$_2$O) λ$_{max}$ 262, λ$_{min}$ 229 nm; IR (CCl$_4$) ν$_{max}$ 1615, 1435 cm$^{-1}$; NMR (CCl$_4$) δ 5.4–6.3 (2H, ABq, 6,7-H's), 4.5 and 5.3 (1H ea, s, 19-H's), 3.7–4.5 (bm, 1,3,20-H's), 3.1–3.7 (bm, NC$\underline{H}_2$, OC$\underline{H}_2$), 0.58 (3H, s, 18-H's).

c) 1α,3β-Dihydroxy-20-epi-23-bis-homo-22-oxa-9,10-secochola-5(Z),7,10(19)-trienic Acid, Piperidine Amide [Formula (I)—A=(A-2), R$^1$+R$^2$=—(CH$_2$)$_5$—, R$^3$=β-CH, R$^4$=R$_5$=H, X=valence bond, Y=O, Z=(CH$_2$)$_3$]

The silylated compound from (b) above (30 mg) was desilylated as in Example 1(c) to give the title diol (12 mg). UV λ$_{max}$ (EtOH) 262, λ$_{min}$ 226 nm; IR ν$_{max}$ (CDCl$_3$) 3100–3620, 1600, 1435 cm$^{-1}$; NMR δ (CDCl$_3$) 5.7–6.6 (2H, ABq, 6,7-H's), 4.8 and 5.3 (1H ea, s, 19-H's), 3.8–4.6 (bm, 1,3,20-H's), 3.2–3.8 (bm, NC$\underline{H}_2$, OC$\underline{H}_2$), 0.63 (3H, s, 18-H's).

EXAMPLE 5 a) 1α,3β-Bis-triisopropylsilyloxy-20β-formyl-9,10-secopregna-5(E) 7,10(19)-triene [Formula (II)—A=(A-3), R$^3$=β-CH$_3$, R$^4$=R$^5$=(i-Pr)$_3$Si, L=CHO]

The 20α-aldehyde obtained by ozonolysis of the 1,3-bis-triisopropylsilyl ether of the sulphur dioxide adduct of 1α-hydroxy vitamin D$_2$ according to GB-A-2114570 (1.34 g) dissolved in benzene (15 ml) and methanol (15 ml) was isomerized by storage overnight with DBU (300 μl) at 0°. The crude product was suspended in ethanol (30 ml), treated with sodium bicarbonate (1.46 g) and heated under reflux with stirring for 2.5 hours to remove the sulphur dioxide. The mixture of aldehydes was resolved by chromatography (silica eluted with 15% benzene in hexane). The first compound eluted was the title(epi)aldehyde (289 mg). UV (Et$_2$O) λ$_{max}$ 269, λ$_{min}$ 227 nm; IR (CCl$_4$) ν$_{max}$ 1620, 1720 cm$^{-1}$; NMR (CCl$_4$) δ 10.0 (1H, d, C$\underline{H}$O), 5.5–6.4 (2H, ABq, 6,7-H's), 4.7–5.0 (2H, bs, 19-H's), 3.8–4.7 (bm, 1,3-H's), 0.57 (3H, s, 18-H's).

b) 1α,3β-Bis-triisopropylsilyloxy-20β-hydroxymethyl-9,10-secopregna-5(E),7,10(19)-triene [Formula (II)—A=(A-3), R$^3$=β-CH$_3$, R$^4$=R$^5$=(i-Pr)$_3$Si, L=CH$_2$OH]

The aldehyde from (a) above (290 mg) in benzene (8 ml) was treated dropwise with sodium borohydride (100 mg) in ethanol (4 ml) at 0° and the reaction mixture stirred at 0° for a further 0.5 hour. After the usual workup the product was purified by chromatography to yield the title alcohol (262 mg). UV (Et$_2$O) λ$_{max}$ 269, λ$_{min}$ 228 nm; IR (CCl$_4$) ν$_{max}$ 1620, 3300–3600 cm$^{-1}$; NMR (CCl$_4$) δ 5.4–6.5 (2H, ABq, 6,7-H's), 4.7–5.0 (2H, bs, 19-H's), 3.7–4.7 (bm, 1,3-H's), 0.57 (3H, s, 18-H's).

c) 1α,3β-Bis-triisoprooylsilyloxy-20-epi-23-homo-23-oxa-9,10-secochola-5(E) 7,10(19)-trienic Acid, Piperidine Amide [Formula (I)—A=(A-3), R$^1$+R$^2$=—(CH$_2$)$_5$—, R$^3$=β—CH$_3$, R$^4$=R$^5$=(i-Pr)$_3$Si, X=CH$_2$, Y=O, Z=CH$_2$]

Potassium t-butoxide (1 ml of a 1M solution in tetrahydrofuran) was added dropwise to a solution of the alcohol from (b) above (131 mg) and 18-crown-6-ether (20 mg) in tetrahydrofuran (1 ml). The mixture was stirred at room temperature for 0.5 hour, then cooled to −10° and treated by dropwise addition of N-(bromoacetyl)piperidine (256 mg) in tetrahydrofuran (1 ml). After a further 10 minutes with stirring the mixture was worked up and the product purified by chromatography to give the title amide (113 mg). UV (Et$_2$O) λ$_{max}$ 270, λ$_{min}$ 231 nm; IR (CCl$_4$) ν$_{max}$ 1645, 1460 cm$^{-1}$; NMR (CCl$_4$) δ 5.4–6.5 (2H, ABq, 6,7-H's), 4.7–5.0 (2H, bs, 19-H's), 3.7–4.7 (bm, 1,3-H's), 2.7–3.7 (m, N—C$\underline{H}_2$—), 0.57 (3H, s, 18-H's).

d) 1α,3β-Bis-triisopropylsilyloxy-20-epi-23-homo-23-oxa-9,10-secochola-5(Z),7,10(19)-trienic Acid, Piperidine Amide [Formula (I)—A=(A-2), R$^1$+R$^2$=—(CH$_2$)$_5$—, R$^3$=β-CH$_3$, R$^4$=R$^5$=(i-Pr)$_3$Si, X=CH$_2$, Y=O, Z=CH$_2$]

The 5(E) compound from (c) above (113 mg) in benzene (14 ml) containing phenazine (54 mg) was photoisomerised as in Example 1(b) (1 hour). The product was purified by chromatography to give 84 mg of the title compound. UV (Et$_2$O) λ$_{max}$ 262, λ$_{min}$ 227 nm; IR (CCl$_4$) ν$_{max}$ 1650, 1465 cm$^{-1}$; NMR (CCl$_4$) δ 5.6–6.3 (2H, ABq, 6,7-H's), 4.8–5.2 (1H ea, bs, 19-H's), 3.6–4.8 (bm, 1,3-H's), 3.0–3.6 (m, N—C$\underline{H}_2$), 0.53 (3H, s, 18-H's).

e) 1α,3β-Dihydroxy-20-epi-23-homo-23-oxa-9,10-secochola-5(Z),7,10(19)-trienic Acid, Piperidine Amide [Formula (I)—A=(A-2), R$^1$+R$^2$=—(CH$_2$)$_5$—, R$^3$=β-CH$_3$, R$^4$=R$^5$=H, X=CH$_2$, Y=O, Z=CH$_2$]

The silyl ether from (d) above (84 mg) in tetrahydrofuran (0.6 ml) was desilylated with tetrabutylammonium fluoride (0.6 ml of 1M solution in tetrahydrofuran) as in Example 1(c). Chromatographic purification of the crude product gave the title compound (43 mg). UV (EtOH) λ$_{max}$ 263, λ$_{min}$ 227 nm; IR (CCl$_4$) ν$_{max}$ 1630, 1450, 3400–3660 cm$^{-1}$; NMR (CDCl$_3$) δ 5.6–6.4 (2H, ABq, 6,7-H's), 4.7, 5.4 (1H ea, bs, 19-H's), 3.8–4.6 (bm, 1,3-H's), 3.0–3.7 (m, N—C$\underline{H}_2$—), 0.92 (d, 21-H's), 0.53 (3H, s, 18-H's).

EXAMPLE 6 a) 1α,3β-Bis-triisoprooylsilyloxy-20α-formyl-9,10-secopregna-5(E),7,10(19)-triene [Formula (II)—A=(A-3), R$^3$=α-CH$_3$, R$^4$=R$^5$=(i-Pr)$_3$Si, L=CHO]

The 20α-aldehyde obtained by ozonolysis of the 1,3-bis-triisopropylsilyl ether of the sulphur dioxide adduct of 1α-hydroxy-vitamin D$_2$ according to GB-A-2114570 (0.49 g) was suspended in n-butanol (10 ml), treated with sodium bicarbonate (0.49 g) and heated at 80° with stirring for 1.5 hours to remove the sulphur dioxide. The aldehyde was purified by chromatography to give the title (normal) aldehyde (330 mg). UV (EtOH) $\lambda_{max}$ 268, $\lambda_{min}$ 228 nm; IR (CCl$_4$) $\nu_{max}$ 1620, 1725 cm$^{-1}$; NMR (CCl$_4$) δ 10.1 (1H, d, CHO), 5.4–6.4 (2H, ABq, 6,7-H's), 4.7–5.0 (2H, bs, 19-H's), 3.8–4.7 (bm, 1,3-H's), 0.6 (3H, s, 18-H's).

b) 1α,3β-Bis-triisopropylsilyloxy-20α-hydroxymethyl-9,10-secopregna-5(E),7,10(19)-triene [Formula (I)—A=(A-3), R$^3$=α-CH$_3$, R$^4$=R$^5$= (i-Pr)$_3$Si, L=CH$_2$OH]

The aldehyde from (a) above (330 mg) in benzene (8 ml) was treated dropwise with sodium borohydride (100 mg) in ethanol (4 ml) at 0 and the reaction mixture stirred at 0° for a further 0.5 hour. After work up the product was purified by chromatography to yield the title alcohol (250 mg). UV (Et$_2$O) $\lambda_{max}$ 269, $\lambda_{min}$ 228 nm; (CCl$_4$) IR $\nu_{max}$ 1620, 3400–3600 cm$^{-1}$; NMR (CCl$_4$) δ 5.5–6.5 (2H, ABq, 6,7-H's), 4.7–5.0 (2H, bs, 19-H's), 3.8–4.7 (bm, 1,3-H's), 0.57 (3H, s, 18-H's).

c) 1α,3β-Bis-triisopropylsilyloxy-23-homo-23-oxa-9,10-secochola-5(E),7,10(19)-trienic Acid, Piperidine Amide [Formula (I)—A=(A-3) R$^1$+R$^2$=—(CH$_2$)$_5$—, R$^3$=α-CH$_3$, R$_4$=R$^5$=(i-Pr)$_3$Si, X=CH$_2$, Y=O, Z=CH$_2$]

Potassium t-butoxide (1 ml of a 1M solution in tetrahydrofuran) was added dropwise to a solution of the alcohol from (b) above (132 mg) and 18-crown-6-ether (20 mg) in tetrahydrofuran (1 ml). The mixture was stirred at room temperature for 0.5 hour, then cooled to −10° and treated by dropwise addition of N-(bromoacetyl)piperidine (258 mg) in tetrahydrofuran (1 ml). After a further 10 minutes with stirring, the mixture was stirred at room temperature for 3 hours, then worked up and the product purified by chromatography to give the title amide (60 mg). UV (Et$_2$O) $\lambda_{max}$ 263, $\lambda_{min}$ 231 nm; IR (CCl$_4$) $\nu_{max}$ 1650, 1475 cm$^{-1}$; NMR (CCl$_4$) δ 5.4–6.4 (2H, ABq, 6,7-H's), 4.7–5.1 (2H, bs, 19-H's), 3.7–4.7 (bm, 1,3-H's), 3.0–3.7 (m, N—CH$_2$—), 0.63 (3H, s, 18-H's).

d) 1α,3β-Bis-triisopropylsilyloxy-23-homo-23-oxa-9,10-secochola-5(Z) 7,10(19)-trienic Acid, Piperidine Amide [Formula (I)—A=(A-2), R$^1$+R$^2$=—(CH$_2$)$_5$—, R$^3$=α-CH$_3$, R$^4$=R$^5$=(i-Pr)Si, X=CH$_2$, Y=O, Z=CH$_2$]

The 5(E) compound from (c) above (60 mg) in benzene (8 ml) containing phenazine (29 mg) was photoisomerised as in Example 1(b) (1 hour). The product was purified by chromatography to give 84 mg of the title compound. UV (Et$_2$O) $\lambda_{max}$ 261, $\lambda_{min}$ 227 nm; IR (CCl$_4$) $\nu_{max}$ 1645, 1455 cm$^{-1}$; NMR (CCl$_4$) δ 5.6–6.4 (2H, ABq, 6,7-H's), 4.6–5.2 (1H ea, bs, 19-H's), 3.7–4.6 (bm, 1,3-H's), 3.0–3.7 (m, N—CH$_2$), 0.53 (3H, s, 18-H's).

e) 1α,3β-Dihydroxy-23-homo-23-oxa-9,10-secochola-5(Z),7,10(19)-trienic Acid, Piperidine Amide [Formula (I)—A=(A-2), R$^1$+R$^2$=—(CH$_2$)$_5$—, R$^3$=α-CH$_3$, R$^4$=R$^5$=H, X=CH$_2$, Y=O, Z=CH$_2$]

The silyl ether from (d) above (40 mg) in tetrahydrofuran (0.3 ml) was desilylated with tetrabutylammonium fluoride (0.6 ml of 1M solution in tetrahydrofuran) as in Example 1(c). Chromatographic purification of the crude product gave the title compound (19 mg). UV (EtOH) $\lambda_{max}$ 262, $\lambda_{min}$ 228 nm; IR (CCl$_4$) $\nu_{max}$ 1640, 1450, 3300–3640 cm$^{-1}$; NMR (CDCl$_3$) δ 5.6–6.5 (2H, ABq, 6,7-H's), 4.7–5.4 (1H ea, bs, 19-H's), 3.8–4.7 (bm, 1,3-H's), 3.0–3.8 (m, N—CH$_2$—), 1.0 (d, 21-H's), 0.52 (3H, s, 18-H's).

The compounds 1α,3β-dihydroxy-23-homo-23-oxa-9,10-secochola-5(Z),7,10(19)-trienic acid, diethylamide [Formula (1)—A=(A-2), R$^1$=R$^2$=Et, R$^3$=α-CH$_3$, R$^4$=R$^5$=H, X=CH$_2$, Y=O, Z=CH$_2$] and 1α,3β-dihydroxy-23-homo-23-oxa-9,10-secochola-5(Z),7,10(19)-trienic acid, cyclopropylamide [Formula (1)—A=(A-2), R$^1$=H, R$^2$=cyclopropyl, R$^3$=α-CH$_3$, R$^4$=R$^5$=H, X=CH$_2$, Y=O, Z=CH$_2$] are prepared by substituting N,N-diethylbromoacetamide and N-cyclopropylbromoacetamide respectively for N-(bromoacetyl)piperidine in Example 6(c) and then following the procedures of Examples 6(d) and 6(e).

The compounds 1α,3β-dihydroxy-23-homo-23-oxa-9,10-secochola-5(E),7-dienic acid, piperidine amide [Formula (1)—A=(A-5), R$^1$+R$^2$=—(CH$_2$)$_5$—, R$^3$=α-CH$_3$, R$^4$=R$^5$=H, X=CH$_2$, Y=O, Z=CH$_2$]; 1α,3β-dihydroxy-23-homo-23-oxa-9,10-secochola-5(Z),7-dienic acid, piperidine amide [Formula (1)—A=(A-4), R$^1$+R$^2$=—(CH$_2$)$_5$—, R$^3$=α-CH$_3$, R$^4$=R$^5$=H, X=CH$_2$, Y=O, Z=CH$_2$]; 1α,3β-dihydroxy-23-homo-23-oxa-10-spirocyclopropyl-9,10-secochola-5(E),7-dienic acid, piperidine amide [Formula (1)—A=(A-7), R$^1$+R$^2$=—(CH$_2$)$_5$—, R$^3$=α-CH$_3$, R$^4$=R$^5$=H, X=CH$_2$, Y=O, Z=CH$_2$]; and 1α,3β-dihydroxy-23-homo-23-oxa-10-spirocyclopropyl-9,10-secochola-5(Z),7-dienic acid, piperidine amide [Formula (1)—A=(A-6), R$^1$+R$^2$=—(CH$_2$)$_5$—, R$^3$=α-CH$_3$, R$^4$=R$^5$=H, X=CH$_2$, Y=O, Z=CH$_2$] are prepared by replacing the sterol in Example 6(c) with 1α,3β-bis-triisopropylsilyloxy-20α-hydroxymethyl-9,10-secopregna-5(E),7-diene (see Preparation 1(b)); 1α,3β-bis-triisopropylsilyloxy-20α-hydroxymethyl-9,10-secopregna-5(Z),7-diene (see Preparation 2); 1α,3β-bis-triisopropylsilyloxy-20α-hydroxymethyl-10-spirocyclopropyl-9,10-secopregna-5(E),7-diene (see Preparation 3(b)); and 1α,3β-bis-triisopropylsilyloxy-20α-hydroxymethyl-10-spirocyclopropyl-9,10-secopregna-5(Z),7-diene (see Preparation 4) respectively and then removing the silyl groups from the products by following the procedure of Example 6(e).

In similar fashion the diethyl (R$^1$=R$^2$=Et) and cyclopropyl (R$^1$=H, R$^2$=cyclopropyl) amide analogues of the above products of Formula (I) having A=(A-4), (A-5), (A-6) or (A-7) are prepared by using N,N-diethylbromoacetamide or N-cyclopropylbromoacetamide respectively in the step analogous to Example 6(c).

In similar fashion the 20-epi analogues of the above compounds (R$^3$=β-CH$_3$) are prepared as above beginning with the corresponding compounds of Formula (II) having R$^3$=β-CH$_3$ and L=CH$_2$OH.

EXAMPLE 7 a) 1α,3β-Bis-triisopropylsilyloxy-23-nor-9,10-secochola-5(E),7,10(19)-trienic Acid, Nitrile (Mixture of 20-normal and 20-epi Isomers) [Formula (I)—A=(A-3), R$^3$=α- and β-CH$_3$, R$^4$=R$^5$= (i-Pr)$_3$Si, L=CH$_2$CN]

A solution of 1α,30-bis-triisopropylsilyloxy-20(α,β)-tosyloxymethyl-9,10-secopregna-5(E),7,10(19)-triene [Formula (II)—A=(A-3), R$^3$=α,β—CH$_3$, R$^4$=R$^5$=(i-Pr)$_3$Si, L=CH$_2$O.tosyl] (1 g) in dimethylsulphoxide (5 ml) containing potassium cyanide (390 mg) was heated at 90° for 2 hours, and the product was extracted (diethyl ether), washed and purified by column chromatography to give the title nitrile (748 mg). UV (Et$_2$O) $\lambda_{max}$ 267, $\lambda_{min}$ 229 nm; NMR (CCl$_4$) δ 5.36–6.13 (ABq, 6,7-H's), 4.83 (bs, 19-H's), 4.13–4.46 (m, 1,3-H's), 0.53 (s, 18-H's).

b) 1α,3β-Bis-triisopropylsilyloxy-23-nor-9,10-secochola-5(E),7,10(19)-trienic Carboxaldehyde. (Mixture of 20-normal and 20-epi Isomers) [Formula (II)—A=(A-3), R$^3$=α- and β-CH$_3$, R$^4$=R$^5$=(i-Pr)$_3$Si—, L=CH$_2$CHO]

The nitrile from (a) above (480 mg) in hexane (3 ml) was cooled to −78° and treated with diisobutylaluminium hydride (1.4 ml of a 1M solution in heptane). The mixture was stirred at 0° for 1 hour, treated with ether and saturated ammonium chloride solution, and the product isolated by extraction into ether. The crude product had UV (Et$_2$O) $\lambda_{max}$ 270, $\lambda_{min}$ 229 nm; IR (CCl$_4$) $v_{max}$ 1730 cm$^{-1}$; NMR (CCl$_4$) δ 10.6 (bs, CHO), 5.53–6.23 (ABq, 6,7-H's), 4.76 (bs, 19-H's), 4.16–4.43 (m, 1,3-H's), 0.56 (s, 18-H's).

c) 1α,3β-Bis-triisopropylsilyloxy-20(α,β)-(2-hydroxyethyl)-9,10-secopregna-5(E),7,10(19)-triene [Formula (II)—A=(A-3), R$^3$=α- and β-CH$_3$, R$^4$=R$^5$=(i-Pr)$_3$Si, L=CH$_2$CH$_2$OH]

The aldehyde from (b) above (440 mg) in benzene (10 ml) was treated at 0° with a solution of sodium borohydride (105 mg) in ethanol (10 ml) followed by stirring at room temperature for 45 minutes. After work up the product was purified by chromatography to give the title compound (380 mg). UV (Et$_2$O) $\lambda_{max}$ 269, $\lambda_{min}$ 228 nm; IR (CCl$_4$) $v_{max}$ 3500–3700 cm$^{-1}$; NMR (CCl$_4$) δ 5.53–6.3 (ABq, 6,7-H's), 4.73 (bs, 19-H's), 4.16–4.43 (m, 1,3-H's), 0.56 (s, 18-H's).

The isomers (at C-20) were resolved at this stage by careful chromatography of 1.2 g of mixture on silica gel developed with 30% benzene in hexane. The 20β-(epi) isomer (145 mg) was less polar and eluted first followed by a mixture of isomers and then the 20α-(normal) isomer (360 mg).

d) 1α,3β-Bis-triisopropylsilyloxy-20α-(2-bromoethyl)-9,10-secopregna-5(E),7,10(19)-triene [Formula (II)—A=(A-3), R$^3$=α-CH$_3$, R$^4$=R$^5$=(i-Pr)$_3$Si, L=CH$_2$CH$_2$Br]

The normal alcohol from (c) above (200 mg) was stirred at room temperature for 2 hours in dichloromethane (5 ml) containing p-toluenesulphonyl chloride (110 mg) and pyridine (243 μl). Sodium bicarbonate (20 ml of a saturated solution) was added, the stirring continued for a further 2 hours, and the reaction mixture worked up. The crude tosylate was dissolved in acetonitrile (6.6 ml) and dichloromethane (6.6 ml) containing lithium bromide (317 mg) and 1,8 bis-dimethylaminonaphthalene ("proton sponge" 40 mg) and the mixture heated under reflux at 80° for 30 minutes. The mixture was then cooled and worked up to give the title bromide (261 mg, purified by chromatography). UV (Et$_2$O) $\lambda_{max}$ 267, $\lambda_{min}$ 228 nm; NMR (CCl$_4$) δ 5.43–6.16 (ABq, 6,7-H's), 4.76 (bs, 19-H's), 4.14–4.45 (m, 1,3-H's), 3.16 (m, CH$_2$Br), 0.5 (s, 18-H's).

e) 1α,3β-Bis-triisopropylsilyloxy-23-homo-9,10-secochola-5(E),7,10(19)-trienic Acid, Piperidine Amide [Formula (I)—A=(A-3), R$^1$+R$^2$=—CH$_2$)$_5$—, R$^3$=α-CH$_3$, R$^4$=R$^5$=(i-Pr)$_3$Si, X=Y=Z=CH$_2$]

N-acetylpiperidine (1.32 ml) in tetrahydrofuran (24.7 ml) was lithiated with lithium diisopropyl amide [prepared from diisopropylamine (2.79 ml) and butyl lithium (6.39 ml of a 1.6M solution in hexane)]. The bromide from (d) above (261 mg) in tetrahydrofuran (1.5 ml) was treated with the above solution (2.75 ml). After 15 minutes the excess reagent was destroyed with ammonium chloride and the mixture worked up to afford the title compound (218 mg after chromatography). UV (Et$_2$O) $\lambda_{max}$ 267, $\lambda_{min}$ 228 nm; IR (CCl$_4$) $v_{max}$ 1620 cm$^{-1}$; NMR (CCl$_4$) δ 5.46–6.23 (ABq, 6,7-H's), 4.73 (bs, 19-H's), 3.33 (nm, n-CH$_2$), 0.53 (s, 18-H's).

f) 1α,3β-Bis-triisopropylsilyloxy-23-homo-9,10-secochola-5(Z) 7,10(19)-trienic Acid, Piperidine Amide [Formula (I)—A=(A-2), R$^1$+R$^2$=—(CH$_2$)$_5$—, R$^3$=α-CH$_3$, R$^4$=R$^5$=(i-Pr)$_3$Si, X=Y=Z=CH$_2$]

The 5(E) compound from (e) above (218 mg) in benzene (2.7 ml) containing phenazine (100 mg) was photoisomerised as in Example I(b) (1 hour). The title compound (142 mg) was isolated by chromatography. UV (Et$_2$O) $\lambda_{max}$ 263, $\lambda_{min}$ 226 nm; IR (CDCl$_3$) $v_{max}$ 1640 cm$^{-1}$; NMR (CDCl$_3$) δ 5.73–6.16 (ABq, 6,7-H's), 5.13, 5.26 (each s, 19-H's), 3.9–4.4 (m, 1,3-H's), 3.43 (nm, n-CH$_2$), 0.53 (s, 18-H's).

g) 1α,3β-Dihydroxy-23-homo-9,10-secochola-5(Z), 7,10(19)-trienic Acid, Piperidine Amide [Formula (I)—A=(A-2), R$^1$+R$^2$=—(CH$_2$)$_5$—, R$^3$=α-CH$_3$, R$^4$=R$^5$=H, X=Y=Z=CH$_2$]

The silyl ether from (f) above (80 mg) in tetrahydrofuran (1 ml) was desilylated with tetrabutylammonium fluoride (1 ml of 1M solution in tetrahydrofuran) at room temperature for 1 hour. The title compound (38 mg) was isolated by preparative TLC. UV (Et$_2$O) $\lambda_{max}$ 263, $\lambda_{min}$ 227 nm; IR (CDCl$_3$) $v_{max}$ 3350–3600, 1640 cm$^{-1}$; NMR (CDCl$_3$) δ 5.7–6.23 (ABq, 6,7-H's), 4.8, 5.13 (each s, 19-H's), 3.83–4.3 (m, 1,3-H's), 3.60 (nm, n-CH$_2$), 0.83–0.93 (d, 21-H's), 0.53 (s, 18-H's).

h) 1α,3β-Dihydroxy-23-homo-9,10-secochola-5(Z), 7-dienic Acid, Piperidine Amide [Formula (I)- A= (A-4), R$^1$+R$^2$=—(CH$_2$)$_5$—, R$^3$=α-CH$_3$, R$^4$=R$^5$=H, X=Y=Z=CH$_2$]

This compound is prepared by hydrogenation of the product of (g) above in accordance with the method of Preparation 1(a) or by similar hydrogenation of the product of (f) above followed by desilylation as described in (g) above.

i) 1α,3β-Dihydroxy-23-homo-9,10-secochola-5(E), 7-dienic Acid, Piperidine Amide [Formula (I)- A= (A-5), R$^1$+R$^2$=—(CH$_2$)$_5$—, R$^3$=α-CH$_3$, R$^4$=R$^5$=H, X=Y=Z=CH$_2$]

This compound is prepared by hydrogenation of the product of (e) above in accordance with the method of Preparation 1(a) followed by desilylation as described in (g) above.

The compounds 1α,3β-dihydroxy-9,10-secochola-5(E),7-dienic acid, piperidine amide [Formula (1)—A=(A-5), R$^1$+R$^2$=—(CH$_2$)$_5$—, R$^3$=α-CH$_3$, R$^4$=R$^5$=H, X=valence bond, Y=Z=CH$_2$]; 1α,3β-dihydroxy-9,10-secochola-5(Z),7-dienic acid, piperidine amide [Formula (1)—A=(A-4), R$^1$+R$^2$=—(CH$_2$)$_5$—, R$^3$=α-CH$_3$, R$^4$=R$^5$=H, X=valence bond, Y=Z=CH$_2$]; 1α,3β-dihydroxy-10-spirocyclopropyl-9,10-secochola-5(E),7-dienic acid, piperidine amide [Formula (I)—A=(A-7), R$^1$+R$^2$=—(CH$_2$)$_5$—, R$^3$=α-CH$_3$, R$^4$=R$^5$=H, X=valence bond, Y=Z=CH$_2$]; and 1α,3β-dihydroxy-10- spirocyclopropyl-9,10-secochola-5(Z),7-dienic acid, piperidine amide [Formula (1)—A=(A-6), $R^1+R^2$=—$(CH_2)_5$—, $R^3$=α-$CH_3$, $R^4$=$R^5$=H, X=valence bond, Y=Z=$CH_2$] are made by substituting for the starting sterol in Example 7(d) 1α,3β-bis-triisopropylsilyloxy-20α-hydroxymethyl-9,10-secopregna-5(E),7-diene (see Preparation 1(b)); 1α,3β-bis-triisopropylsilyloxy-20α-hydroxymethyl-9,10-secopregna-5(Z),7-diene (see Preparation 2); 1α,3β-bis-triisopropylsilyloxy-20α-hydroxymethyl-10-spirocyclopropyl-9,10-secopregna-5(E),7-diene (see Preparation 3(b)); and 1α,3β-bis-triisopropylsilyloxy-20α-hydroxymethyl-10-spirocyclopropyl-9,10-secopregna-5(Z),7-diene (see Preparation 4) respectively and then following the procedure of Example 7(e) and finally removing the silyl groups from the products by following the procedure of Example 7(g).

In a similar fashion the compounds 1α,3β-dihydroxy-23-homo-9,10-secochola-5(E),7-dienic acid, piperidine amide [Formula (1)—A=(A-5), $R^1+R^2$=—$(CH_2)_5$—, $R^3$=α-$CH_3$, $R^4$=$R^5$=H, X=Y=Z=$CH_2$]; 1α,3β-dihydroxy-23-homo-9,10-secochola-5(Z),7-dienic acid, piperidine amide [Formula (1)—A=(A-4), $R^1+R^2$=—$(CH_2)_5$—, $R^3$=α-$CH_3$, $R^4$=$R^5$=H, X=Y=Z=$CH_2$]; 1α,3β-dihydroxy-23-homo-10-spirocyclopropyl-9,10-secochola-5(E),7-dienic acid, piperidine amide [Formula (1)—A=(A-7), $R^1+R^2$=—$(CH_2)_5$—, $R^3$=α-$CH_3$, $R^4$=$R^5$=H, X=Y=Z=$CH_2$]; 1α,3β-dihydroxy-23-homo-10-spirocyclopropyl-9,10-secochola-5(Z),7-dienic acid, piperidine amide [Formula (1)—A=(A-6), $R^1+R^2$=—$(CH_2)_5$—, $R^3$=α-$CH_3$, $R^4$=$R^5$=H, X=Y=Z=$CH_2$]; and 1α,3β-dihydroxy-23-homo-19-nor-9,10-secochola-5,7-dienic acid, piperidine amide [Formula (1)—A=(A-8), $R^1+R^2$=—$(CH_2)_5$—, $R^3$=α-$CH_3$, $R^4$=$R^5$=H, X=Y=Z=$CH_2$]; are prepared by tosylating the following intermediates respectively according to Example 7(d) and then applying the procedures of Example 7(a), 7(b), 7(c), 7(d) and 7(e) and desilylating according to Example 7(g): 1α,3β-bis-triisopropylsilyloxy-20α-hydroxymethyl-9,10-secopregna-5(E),7-diene (see Preparation 1(b)); 1α,3β-bis-triisopropylsilyloxy-20α-hydroxymethyl-9,10-secopregna-5(Z),7-diene (see Preparation 2); 1α,3β-bis-triisopropylsilyloxy-20α-hydroxymethyl-10-spirocyclopropyl-9,10-secopregna-5(E),7-diene (see Preparation 3(b)); 1α,3β-bis-triisopropylsilyloxy-20α-hydroxymethyl-10-spirocyclopropyl-9,10-secopregna-5(Z),7-diene (see Preparation 4); and 1α,3β-bis-triisopropylsilyloxy-20α-hydroxymethyl-19-nor-9,10-secopregna-5,7-diene [Formula (II)—A=(A-8), $R^3$=α-$CH_3$, $R^4$=$R^5$=(i-Pr)$_3$Si, L=$CH_2OH$].

EXAMPLE 8 a) 1α,3β-Bis-triisopropylsilyloxy-20β-(2-bromoethyl)-9,10-secopregna-5(E),7,10(19)-triene [Formula (II)—A=(A-3), $R^3$=β-$CH_3$, $R^4$=$R^5$=(i-Pr)$_3$Si, L=$CH_2CH_2Br$]

The epi-alcohol from Example 7(c) above [Formula II—A=(A-3), $R^3$=β-$CH_3$, $R^4$=$R^5$=(i-Pr)$_3$Si, L=$CH_2CH_2OH$] (200 mg) was converted following the procedure of Example 7(d) into the corresponding bromide, the title compound (248 mg). UV (Et$_2$O) $\lambda_{max}$ 269, $\lambda_{min}$ 227 nm; NMR (CCl$_4$) δ 5.46–6.23 (ABq, 6,7-H's), 4.7, (bs, 19-H's), 4.13–4.4 (m, 1,3-H's), 3.16 (m, CH$_2$Br), 0.56 (s, 18-H's).

b) 1α,3β-Bis-triisopropylsilyloxy-20-epi-23-homo-9,10-secochola-5(E),7,10(19)-trienic Acid, Piperidine Amide [Formula (I)—A=(A-3), $R^1+R^2$= —$(CH_2)_5$—, $R^3$=β-$CH_3$, $R^4$=$R^5$=(i-Pr)$_3$Si, X=Y=Z= $CH_2$]

The epi-bromide from (a) above (248 mg) was treated with the lithium salt of N-acetylpiperidine as in Example 7(e) to give the title compound (211 mg). UV (Et$_2$O) $\lambda_{max}$ 269, $\lambda_{min}$ 229 nm; IR (CCl$_4$) $v_{max}$ 1640 cm$^{-1}$; NMR (CDCl$_3$) δ 5.56–6.23 (ABq, 6,7-H's), 4.83, (bs, 19-H's), 3.36 (nm, n-CH$_2$), 0.53 (s, 18-H's).

c) 1α,3β-Bis-triisopropylsilyloxy-20-epi-23-homo-9,10-secochola-5(Z),7,10(19)-trienic Acid, Piperidine Amide [Formula (I)—A=(A-2), $R^1+R^2$= —$(CH_2)_5$—, $R^3$=β-$CH_3$, $R^4$=$R^5$=(i-Pr)$_3$Si—, X=Y= Z=$CH_2$]

The 5(E) compound from (b) above (211 mg) in benzene (2.7 ml) containing phenazine (100 mg) was photoisomerised as in Example 1(b) (1 hour). The title compound (142 mg) was isolated by chromatography. UV (Et$_2$O) $\lambda_{max}$ 263, $\lambda_{min}$ 227 nm; IR (CCl$_4$) $v_{max}$ 1650 cm$^{-1}$; NMR (CDCl$_3$) δ 5.5–6.4 (ABq, 6,7-H's), 4.76, 5.1 (each s, 19-H's), 4.1–4.3 (m, 1,3-H's), 3.4 (nm, n-C$\underline{H}_2$), 0.53 (s, 18-H's).

d) 1α,3β-Dihydroxy-20-epi-23-homo-9,10-secochola-5(Z),7,10(19)-trienic Acid, Piperidine Amide [Formula (I)—A=(A-2), $R^1+R^2$=— $(CH_2)_5$—, $R^3$=β-$CH_3$, $R^4$=$R^5$=H, X=Y=Z=$CH_2$]

The silyl ether from (c) above (80 mg) in tetrahydrofuran (1 ml) was desilylated with tetrabutylammonium fluoride (1 ml of 1M solution in tetrahydrofuran) at room temperature for 1 hour. The title compound (35 mg) was isolated by preparative TLC. UV (Et$_2$O) $\lambda_{max}$ 264, $\lambda_{min}$227 nm; IR (CCl$_4$) $v_{max}$ 3350–3600, 1620 cm$^{-1}$; NMR (CDCl$_3$) δ 5.63–6.2 (ABq, 6,7-H's), 4.76, 5.1 (each s, 19-H's), 3.86–4.2 (m, 1,3-H's), 3.3 (nm, n-C$\underline{H}_2$), 0.76–0.86 (d, 21-H's), 0.53 (s, 18-H's).

e) 1α,3β-Dihydroxy-20-epi-23-homo-9,10-secochola-5(Z),7-dienic Acid, Piperidine Amide [Formula (I)—A=(A-4), $R^1+R^2$=—$(CH_2)_5$—, $R^3$=β-$CH_3$, $R^4$=$R^5$=H X=Y=Z=$CH_2$]

This compound is prepared by hydrogenation of the product of (d) above in accordance with the method of Preparation 1(a) or by similar hydrogenation of the product of (c) above followed by desilylation as described in (d) above.

f) 1α,3β-Dihydroxy-20-epi-23-homo-9,10-secochola-5(E),7-dienic Acid, Piperidine Amide [Formula (I)—A=(A-5), $R^1+R^2$=—$(CH_2)_5$—, $R^3$=β-$CH_3$, $R^4$=$R^5$=H, X=Y=Z=$CH_2$]

This compound is prepared by hydrogenation of the product of (b) above followed by desilylation as described in (d) above.

EXAMPLE 9 a) 1α,3β-Bis-triisopropylsilyloxy-20-epi-23-homo-9,10-seco-23-thiachola-5(E),7,10(19)-trienic Acid, Ethyl Ester [Formula (II)—A=(A-3), $R^3$=β-$CH_3$, $R^4$=$R^5$=(i-Pr)$_3$Si, L=$CH_2.S.CH_2.CO.OEt$]

A solution of the 20-epi alcohol from Example 5(b) (131 mg) in dichloromethane (3 ml) containing "proton sponge" (171 mg) was treated at −78° with trifluoromethanesulphonic anhydride (68 mg). The reaction mixture was allowed to warm to room temperature, returned to −78°, treated with ethyl 2-mercaptoethanoate (72 mg, added dropwise), allowed to warm to room temperature and stirred for a further hour. Following work-up the product was purified by chromatography to give the title compound (75 mg). UV (Et$_2$O), $\lambda_{max}$ 268, $\lambda_{min}$ 228 nm; IR (CCl$_4$) $v_{max}$ 1740, 1630 cm$^{-1}$; NMR (CCl$_4$) $\delta$ 5.4–6.7 (ABq, 6,7-H's), 4.7–5.0 (bs, 19-H's), 3.8–4.7 (m, q, 1,3-H's, Et-H's), 2.96 (s, S—C$\underline{H}_2$—CO$_2$Et), 0.57 (s, 18-H's).

b) 1α,3β-Bis-triisopropylsilyloxy-20-epi-23-homo-9,10-seco-23-thiachola-5(E),7,10(19)-trienic Acid, Piperidine Amide [Formula (I)—A=(A-3), R$^1$+R$^2$= —(CH$_2$)$_5$—, R$^3$=β-CH$_3$, R$^4$=R$^5$=(i-Pr)$_3$Si, X=CH$_2$, Y=S, Z=CH$_2$]

A solution of the ester from (a) above (62 mg) in hexane (1 ml) was treated at −78° by dropwise addition of a reagent prepared from piperidine (34 mg) and Sn[N(TMS)$_2$]$_2$ (176 mg) in hexane (2.1 ml). The reaction mixture was then allowed to warm to room temperature and stirred for 1 hour. The tin was precipitated with methanol, the reaction worked up and the product purified by chromatography to give the title compound (47 mg). UV (Et$_2$O) $\lambda_{max}$ 210, 269, $\lambda_{min}$ 230 nm; IR (CCl$_4$) $v_{max}$ 1645, 1465 cm$^{-1}$; NMR (CCl$_4$) $\delta$ 5.4–6.6 (ABq, 6,7-H's), 4.7–5.0 (bs, 19-H's), 3.7–4.7 (m, 1,3-H's), 3.2–3.7 (m, N—C$\underline{H}_2$'s), 3.07 (s, S—C$\underline{H}_2$—CO$_2$Et), 0.6 (s, 18-H's).

c) 1α,3β-Dihydroxy-20-epi-23-homo-9,10-seco-23-thiachola-5(Z) 7,10(19)-trienic Acid, Piperidine Amide [Formula (I)—A=(A-2), R$^1$+R$^2$=—(CH$_2$)$_5$—, R$^3$=β-CH$_3$; R$^4$=R$^5$=H, X=CH$_2$, Y=S, Z=CH$_2$]

The 5(E) compound from (b) above (47 mg) was photoisomerised as in Example 1(b) to give the 5(Z) compound (38 mg). UV (Et$_2$O) $\lambda_{max}$ 210, 264, $\lambda_{min}$ 229 nm; IR (CCl$_4$) $v_{max}$ 1645, 1455 cm$^{-1}$; NMR (CCl$_4$) $\delta$ 5.6–6.4 (ABq, 6,7-H's), 4.7, 5.3 (each s, 19-H's), 3.9–4.7 (m, 1,3-H's), 3.1–3.6 (m, N—C$\underline{H}_2$'s), 3.07 (s, S—CH$_2$—CO$_2$Et), 0.53 (s, 18-H's). This was desilylated as in Example 1(c) to give the title compound (19 mg, purified by chromatography). UV (EtOH) $\lambda_{max}$ 209, 264, $\lambda_{min}$ 230 nm; IR (CDCl$_3$) $v_{max}$ 3200–3660, 1630, 1450 cm$^{-1}$; NMR (CDCl$_3$) $\delta$ 5.4–6.5 (ABq, 6,7-H's), 4.7 and 5.4 (each s, 19-H's), 3.7–4.7 (m, 1,3-H's), 3.0–3.7 (m, N—C$\underline{H}_2$, S—C$\underline{H}_2$), 0.97 (d, j=6 Hz, 21-H's), 0.55 (s, 18-H's).

The compound 23-aza-1α,3β-dihydroxy-20-epi-23-bis-homo-9,10-secochola-5(Z),7,10(19)-trienic Acid, Piperidine Amide [Formula (I)—A=(A-2), R$^1$+R$^2$=—(CH$_2$)$_5$—, R$^3$=β-CH$_3$, R$^4$=R$^5$=H, X=CH$_2$, Y=NH, Z=(CH$_2$)$_2$] is prepared in a similar fashion substituting N-(β-alanyl)-piperidine (8 equivalents) for the mercaptoethanoate ester, then photoisomerising according to Example 1(b) and desilylating according to Example 1(c).

The compound 23-aza-1α,3β-dihydroxy-20-epi-23-homo-9,10-secochola-5(Z),7,10(19)-trienic acid, piperidine amide [Formula (I)—A=(A-2), R$^1$+R$^2$=—(CH$_2$)$_5$—, R$^3$=β-CH$_3$, X=CH$_2$, Y=NH, Z=CH$_2$] was similarly prepared by substituting N-glycylpiperidine (8 equivalents) for the N-(β-alanayl)piperidine. Reaction of the 20-epi alcohol (120 mg) afforded the 5(E) silyl compound (60 mg): UV (Et$_2$O) $\lambda_{max}$ 204, 269, $\lambda_{min}$ 230 nm; IR (CDCl$_3$) $v_{max}$ 1640, 1460, 1440 cm$^{-1}$; NMR (CDCl$_3$) $\delta$ 5.5–6.6 (ABq, 6,7-H's), 4.9–5.0 (bs, 19-H's), 3.8–4.9 (m, 1,3-H's), 3.0–3.7 (m, H's adjacent to N), 0.53 (s, 18-H's). Isomerisation afforded the corresponding 5(Z) silyl compound (50 mg): UV (Et$_2$O) $\lambda_{max}$ 207, 263, $\lambda_{min}$ 227 nm; IR (CDCl$_3$) $v_{max}$ 1630, 1460, 1440 cm$^{-1}$; NMR (CDCl$_3$) $\delta$ 5.6–6.5 (ABq, 6,7-H's), 4.7, 5.3, (each s, 19-H's), 3.9–4.7 (m, 1,3-H's), 3.0–3.7 (m, H's adjacent to N), 0.53 (s, 18-H's). Desilylation afforded the desired 1α,3β-dihydroxy compound (10 mg): UV (EtOH) $\lambda_{max}$ 207, 263, $\lambda_{min}$ 227 nm; IR (CDCl$_3$) $v_{max}$ 3660–3100, 1630, 1440 cm$^{-1}$; NMR (CDCl$_3$) $\delta$ 5.7– 6.5 (ABq, 6,7-H's), 4.8, 5.4 (each s, 19-H's), 3.8–4.6 (m, 1,3-H's), 3.0–3.8 (m, H's adjacent to N), 0.97 (d, 21-H's), 0.53 (s, 18-H's).

EXAMPLE 10 a) 1α,3β-Bis-t-butyldimethylsilyloxy-20β-hydroxymethyl-19-nor-9,10-secopregna-5(E),7-diene [Formula (II)—A=(A-8), R$^3$=β-CH$_3$, R$^4$=R$^5$= t-Bu(Me)$_2$Si, L=CH$_2$OH]

1α,3β-Bis-t-butyldimethylsilyloxy-20α-formyl-19-nor-9,10-secopregna-5,7-diene [Formula (II)—A=(A-8), R$^3$=α-CH$_3$, R$^4$=R$^5$=t-Bu(Me)$_2$Si, L=CHO], obtained as in Tetrahedron Lett. (1992), 33, p 2937, (about 1.5 g) is dissolved in benzene (15 ml) and methanol (15 ml) and isomerised by storage overnight with DBU (400 µl) at 0°. The mixture of normal (20α-formyl) and epi (20β-formyl) aldehydes may be resolved by chromatography (silica eluted with 15% benzene in hexane) before or after reduction of the aldehyde (ca 1 g) in benzene (30 ml) by dropwise treatment with sodium borohydride, (400 mg) in ethanol (15 ml) at 0°, whereafter the reaction mixture is stirred at 0° for a further 0.5 hour. After work up the product is resolved by chromatography (silica gel eluting with benzene or ether in hexane) to yield the title compound.

b) 1α,3β-Bis-t-butyldimethylsilyloxy-20-epi-19-nor-9,10-secochola-5,7-dienic Acid, Piperidine Amide [Formula (I)—A=(A-8), R$^1$+R$^2$=—(CH$_2$)$_5$—, R$^3$=β-CH$_3$, R$^4$=R$^5$=t-Bu(Me)$_2$Si, X=valence bond, Y=Z=CH$_2$]

The epi-alcohol from (a) above (200 mg) is stirred at room temperature for 2 hours in dichloromethane (5 ml) containing p-toluenesulphonyl chloride (110 mg) and pyridine (243 µl), Sodium bicarbonate (20 ml of a saturated solution) is added, the stirring continued for a further 2 hours, and the reaction mixture worked up. The crude tosylate is dissolved in acetonitrile (6.6 ml) and dichloromethane (6.6 ml) containing lithium bromide (317 mg) and 1,8 bis-dimethylaminonaphthalene ("proton sponge"—40 mg) and the mixture heated under reflux at 80° for 30 minutes. The mixture is then cooled and worked up to give the corresponding 20-bromomethyl compound which is dissolved in tetrahydrofuran (1.5 ml) and treated at −78° with a solution of lithio-N-acetylpiperidine (2.75 ml) prepared by lithiating N-acetylpiperidine (1.32 ml) in tetrahydrofuran (24.7 ml) with lithium diisopropyl amide [prepared from diisopropylamine (2.79 ml) and butyl lithium (6.39 ml of a 1.6M solution in hexane)]. The reaction mixture is allowed to warm to room temperature and after 15 minutes the excess reagent is destroyed with ammonium chloride and the mixture worked up to afford the title compound.

c) 1α,3β-Dihydroxy-20-epi-19-nor-9,10-secochola-5,7-dienic Acid, Piperidine Amide [Formula (I)—A=(A-8), R$^1$+R$^2$=—(CH$_2$)—, R$^3$=β-CH$_3$, R$^4$=R$^5$= H, X=valence bond, Y=Z=CH$_2$]

The silyl ether from (b) above (about 100 mg) in tetrahydrofuran (1.5 ml) is desilyated with tetrabutylammonium fluoride (1.3 ml of a 1M solution in tetrahydrofuran) at room temperature for 1 hour. The title compound is isolated by chromatography.

EXAMPLE 11 a) 1α,3β-Bis-t-butyldimethylsilyloxy-23-homo-19-nor-23-oxa-9,10-secochola-5,7-dienic Acid, Piperidine Amide [Formula (I)—A=(A-8), R$^1$+R$^2$= —(CH$_2$)$_5$—, R$^3$=α-CH$_3$, R$^4$=R$^5$=t-Bu(Me)$_2$Si, X= CH$_2$, Y=O, Z=CH$_2$]

Potassium t-butoxide (1.2 ml of a 1M solution in tetrahydrofuran) is added dropwise to a solution of 1α,3β- bis-t-butyldimethylsilyloxy-20α-hydroxymethyl-9,10-secopregna-5,7-diene (*Tetrahedron Lett*, (1992), 33, p 2937) (about 150 mg) and 18-crown-6-ether (25 mg) in tetrahydrofuran (1 ml). The mixture is stirred at room temperature for 0.5 hour, then cooled to −10° and treated by dropwise addition of N-(bromoacetyl)piperidine (256 mg) in tetrahydrofuran (1 ml). After a further 10 minutes with stirring, the mixture is worked up and the product purified by chromatography to give the title compound.

b) 1α,3β-Dihydroxy-23-homo-19-nor-23-oxa-9,10-secochola-5,7-dienic Acid, Piperidine Amide [Formula (I)—A=(A-8) $R^1+R^2$=—$(CH_2)_5$—, $R^3$=α-$CH_3$, $R^4$=$R^5$=H, X=$CH_2$, Y=O, Z=$CH_2$]

The silyl ether from (a) above (80 mg) in tetrahydrofuran (0.6 ml) is desilylated with tetrabutylammonium fluoride (0.6 ml of a 1M solution in tetrahydrofuran) as in Example 1(c). Chromatographic purification of the crude product gives the title compound.

EXAMPLE 12

23-Aza-1α,3β-dihydroxy-9,10-secochola-5(Z),7,10(19)-trienic Acid, Piperidine Amide [Formula (I)—A=(A-2), $R^1+R^2$=—$(CH_2)_5$—, $R^3$=α-$CH_3$, $R^4$=$R^5$=H, X=$CH_2$, Y=NH, Z=valence bond.]

20α-Aminomethyl-1α,3β-bis-triisopropylsilyloxy-9,10-secopregna-5(E),7,10(19)-diene [Formula (II)—A=(A-3), $R^3$=α-$CH_3$, $R^4$=$R^5$=(i-Pr)$_3$Si, L=$CH_2NH_2$] is dissolved in tetrahydrofuran and acylated with N-chloroformylpiperidine (1.2 equivalents) to give 1α,3β-bis-triisopropylsilyloxy-23-aza-9,10-secopregna-5(E),7,10(19)-trienic acid, piperidine amide [Formula (I)—A=(A-3), $R^1+R^2$+—$(CH_2)_5$—, $R^3$=α-$CH_3$, $R^4$=$R^5$=(i-Pr)$_3$Si, X=$CH_2$, Y=NH, Z=valence bond]. The product is photoisomerised as in Example 1(b) and the silyl groups are removed as in Example 1(c) to give the title compound.

EXAMPLE 13 a) Mixture of 22-aza-1α,3β-bis-triisopropylsilyloxy-23-homo-9,10-secochola-5(E) 7,10(19)-trienic Acid, Piperidine Amide and Its 20-epimer [Formula (I)—A=(A-3), $R^1+R^2$=—$(CH_2)_5$—, $R^3$=α,β-$CH_3$, $R^4$=$R^5$, =(i-Pr)$_3$Si, X=valence bond, Y=NH, Z=$(CH_2)_2$]

A mixture of 1α,3β-bis-triisopropylsilyloxy-9,10-secopregna-5(E),7,10(19)-trien-20-one (248 mg), titanium (IV) isopropoxide (682 mg) and N-(R-alanyl)piperidine (187 mg) were stirred for 3 hours at room temperature. Ethanol (1 ml) and sodium cyanoborohydride (38 mg) were added and stirring was continued overnight. Following work up the title products were resolved by chromatography on an alumina column. The less polar isomer (presumably the 20-epi) (170 mg) had UV (Et$_2$O) $\lambda_{max}$ 208, 269, $\lambda_{min}$ 230 nm; IR (CDCl$_3$) $v_{max}$ 1625, 1450 cm$^{-1}$: NMR (CDCl$_3$) δ 5.5–6.8 (ABq, 6,7-H's), 4.8–5.1 (bs, 19-H's), 4.0–4.8 (m, 1,3-H's), 3.1–3.7 (m, H's adjacent to N), 0.58 (s, 18-H's). The more polar (minor) isomer (96 mg) had UV (Et$_2$O) $\lambda_{max}$ 208, 268, $\lambda_{min}$ 229 nm; IR (CDCl$_3$) $v_{max}$1630, 1450 cm$^{-1}$; NMR (CDCl$_3$) δ 5.5–6.5 (ABq, 6,7-H's), 4.7–5.0 (bs, 19-H's), 3.8–4.7 (m, 1,3-H's), 3.1–3.8 (m, H's adjacent to N), 0.53 (s, 18-H's).

b) 22-Aza-1α,3β-bis-triisopropylsilyloxy-20-epi-23-homo-9,10-secochola-5(Z),7,10(19)-trienic Acid, Piperidine Amide [Formula (I)—A=(A-2), $R^1+R^2$= —$CH_2$)—, $R^3$=β-$CH_3$, $R^4$=$R^5$, =(i-Pr)$_3$Si, X=valence bond, Y=NH, Z=$(CH_2)_2$]

The major, less polar isomer from (a) above (95 mg) was photoisomerised as in Example 1(b) to give the title compound (65 mg). UV (Et$_2$O) $\lambda_{max}$ 207, 263, $\lambda_{min}$ 227 nm; IR (CDCl$_3$) $v_{max}$ 1620, 1450 cm$^{-1}$; NMR (CDCl$_3$) δ 5.6–6.4 (ABq, 6,7-H's), 4.7, 5.3 (each s, 19-H's), 3.1–3.7 (H's adjacent to N), 0.57 (s, 18-H's).

c) 22-Aza-1α,3β-dihydroxy-20-epi-23-homo-9,10-secochola-5(Z) 7,10(19)-trienic Acid, Piperidine Amide [Formula (I)—A=(A-2), $R^1+R^2$=—$(CH_2)$-, $R^3$=β-$CH_3$, $R^4$=$R^5$=H, X=valence bond, Y=NH, Z=$(CH_2)_2$]

The silyl ether from (b) above (65 mg) was desilylated as in Example 1(c). Passage through a neutral alumina column followed by preparative TLC (alumina plates) gave the title compound (17 mg). UV (EtOH) $\mu_{max}$ 206, 262, $\lambda_{min}$ 228 nm; IR (CDCl$_3$) $v_{max}$ 3640–3200, 1615, 1440 cm$^{-1}$; NMR (CDCl$_3$) δ 5.5–6.4 (ABq, 6,7-H's), 4.7, 5.3 (each s, 19-H's), 3.7–4.7 (m, 1,3-H's), 3.0–3.7 (m, H's adjacent to N), 1.17 (d, 21-H's), 0.63 (s, 18-H's).

EXAMPLE 14 a) 20α-Aminomethyl-1α,3β-bis-triisopropylsilyloxy-9,10-secoprepna-5(E),7,10(19)-triene [Formula (II)—A=(A-3), L=$CH_2NH_2$, $R^3$=α-$CH_3$, $R^4$=$R^5$=(i-Pr)$_3$Si]

A solution of the corresponding 20α-azidomethyl compound (L=$CH_2N_3$) (247 mg) in ether (0.75 ml) was treated with lithium aluminium hydride (1.9 ml of 1M solution) at 0°. The reaction mixture was stirred at room temperature for 45 minutes, then cooled to 0°, diluted with diethyl ether, treated with wet sodium sulphate and filtered. The filtrate was washed with water and brine, then evaporated to give the title compound (208 mg). UV (Et$_2$O) $\lambda_{max}$ 269, $\lambda_{min}$ 228 nm.

b) 23-Aza-1α,3β-bis-triisopropylsilyloxy-9,10-secochola-5(E) 7,10(19)-trienic Acid, Diethyl Amide [Formula (I)—A=(A-3), $R^1$=$R^2$=$C_2H_5$, $R^3$= α-$CH_3$, $R^4$=$R^5$=(i-Pr)$_3$Si, X=$CH_2$, Y=NH, Z= valence bond]

A solution of the 20α-aminomethyl compound from (a) above (204 mg) in tetrahydrofuran (1.0 ml) was treated with 10% aqueous sodium hydroxide (0.720 ml), cooled to 0°, treated with N,N-diethylcarbamoyl chloride (80 μl), then stirred at room temperature for 4 hours. The crude product was extracted into ether and worked up. Chromatography gave the title product (164 mg). UV (Et$_2$O) $\mu_{max}$ 269, $\lambda_{min}$ 228 nm; IR (CCl$_4$) $v_{max}$ 1650 cm$^{-1}$; NMR (CCl$_4$) δ6.26–5.5 (ABq, 6,7-H's), 4.73 (s, 19-H's), 4.46–4 (m, 1,3-H's), 0.53 (s, 18-H's).

c) 23-Aza-α,3β-bis-triisopropylsilyloxy-9,10-secochola-5(Z),7,10(19)-trienic Acid, Diethyl Amide [Formula (I)—A=(A-2), $R^1$=$R^2$=$C_2H$, $R^3$=α-$CH_3$; $R_4$=$R^5$=(i-PR)$_3$Si, X=$CH_2$, Y=NH, Z=valence bond]

The 5(E) compound from (c) above (160 mg) in benzene (22 ml) containing phenazine (80 mg) was irradiated for 75 minutes. The solvent was removed and the title product (102 mg) isolated by preparative TLC. UV (Et$_2$O) $\lambda_{max}$ 262–3, $\lambda_{min}$ 226 nm; IR (CCl$_4$) $v_{max}$ 1650 cm$^{-1}$; NMR (CCl$_4$) δ 5.7–5.93 (ABq 6,7-H's), 4.6, 4.96 (each s, 19-H's), 0.56 (s, 18-H's).

d) 23-Aza-α,3β-dihydroxy-9,10-secochola-5(Z),7,10(19)-trienic Acid, Diethyl Amide [Formula (I)—A= (A-2), $R^1$=$R^2$=$C_2H_5$, $R^3$=α-$CH_3$, $R^4$=$R^5$=H, X= $CH_2$, Y=NH, Z=valence bond]

The silyl ether from (c) above (102 mg) in tetrahydrofuran (0.7 ml) was desilylated by treatment with tetrabutylammonium fluoride (0.7 ml of 1M solution in tetrahydrofuran) at room temperature for 5 hours. The title product (35.8 mg) was isolated by preparative TLC (2×). UV (EtOH) $\lambda_{max}$ 26, $\lambda_{min}$ 226 nm; IR (CDCl$_3$) $\nu_{max}$ 1630, 3200–3600 cm$^{-1}$; NMR (CDCl$_3$) δ 5.76–6.36 (ABq, 6,7-H's), 4.8, 5.2 (each s, 19-H's), 3.0–3.3 (m, H's adjacent to N), 0.9–1.23 (m, 21-H's, Me H's of ethyl), 0.53 (s, 18-H's).

EXAMPLE 15 a) Mixture of 20α- and 20β-aminomethyl-1α,38-bis-triisopropylsilyloxy-9,10-secopregna-5(E),7,10 (19)-triene [Formula (II)—A=(A-3), L=CH$_2$NH$_2$, R$^3$=α,β-CH$_3$, R$^4$=R$^5$=(i-Pr)$_3$-Si]

A solution of the corresponding 20α,β-azidomethyl compound (L=CH$_2$N$_3$) (170 mg) in ether (0.5 ml) was treated with lithium aluminium hydride (1.36 ml of 1M solution) at 0°. The reaction mixture was stirred at room temperature for 45 minutes, then cooled to 0°, diluted with diethyl ether, treated with wet sodium sulphate and filtered. The filtrate was washed with water and brine, then evaporated to give the title compound (109 mg). UV (Et$_2$O) $\lambda_{max}$ 268, $\lambda_{min}$ 228 nm.

b) 23-Aza-1α,3β-bis-triisopropylsilyloxy-9,10-secochola-5(E),7,10(19)-trienic Acid, Diethyl Amide and Its 20-epimer [Formula (I)—A=(A-3), R$^1$=R$^2$=CH$_2$H$_5$, R$^3$=α,β-CH$_3$, R$^4$=R$^5$=(i-Pr)$_3$Si, X=CH$_2$, Y=NH, Z=valence bond]

A solution of the 20α,β-aminomethyl compound from (a) above (102 mg) in tetrahydrofuran (0.5 ml) was treated with 10% aqueous sodium hydroxide (0.360 ml), cooled to 0°,treated with N,N-diethylcarbamoyl chloride (39 μl), then stirred at room temperature for 3 hours. The crude product was extracted into ethyl acetate and worked up. Chromatography gave two products, the less polar of which is presumed to be the 20-epi compound (45 mg) which had UV (Et$_2$O) $\lambda_{max}$ 268, $\lambda_{min}$ 228 nm; IR (CCl$_4$) $\nu_{max}$ 1650 cm$^{-1}$; NMR (CCl$_4$) δ 6.3–5.56 (ABq, 6,7-H's), 4.8 (s, 19-H's), 4.36–4.03 (m, 1,3-H's), 3.0–3.3 (m, H's adjacent to N), 0.56 (s, 18-H's).

c) 23-Aza-1α,3β-bis-triisopropylsilyloxy-20-epi-9,10-secochola-5(Z),7,10(19)-trienic Acid, Diethyl Amide [Formula (I)—A=(A-2), R$^1$=R$^2$=C$_2$H$_5$, R$^3$=β-CH$_3$, R$^4$=R$^5$=(i-Pr)$_3$Si, X=CH$_2$, Y=NH, Z=valence bond]

The 5(E) compound from (b) above (45 mg) in benzene (11 ml) containing phenazine (38 mg) was irradiated for 75 minutes and processed as in Example 14(c). The title product (102 mg) was isolated by preparative TLC. UV (Et$_2$O) $\lambda_{max}$ 262, $\lambda_{min}$ 227 nm; IR (CCl$_4$) $\nu_{max}$ 1640 cm$^{-1}$; NMR (CCl$_4$) δ 5.56–5.9 (ABq, 6,7-H's), 4.59, 4.96 (each s, 19-H's), 3.96–4.3 (m, 1,3-H's), 2.9–3.23 (m, H's adjacent to N), 0.56 (s, 18-H's).

d) 23-Aza-1α,3β-dihydroxy-20-epi-9,10-secochola-5(Z),7,10(19)-trienic Acid, Diethyl Amide [Formula (I)—A=(A-2), R$^1$=R$^2$=C$_2$H$_5$, R$^3$=β-CH$_3$, R$^4$=R$^5$=H, X=CH$_2$, Y=NH, Z=valence bond]

The silyl ether from (c) above (32 mg) in tetrahydrofuran (0.35 ml) was desilylated as in Example 14(d) by treatment with tetrabutylammonium fluoride (0.35 ml) of 1M solution in tetrahydrofuran). Work up and chromatography gave the title product (6 mg) isolated by further chromatography on deactivated alumina. UV (EtOH) $\lambda_{max}$ 263, $\lambda_{min}$ 227 nm; IR (CDCl$_3$) $\nu_{max}$ 1630, 3400 cm$^{-1}$; NMR (CDCl$_3$) δ 5.76–6.33 (ABq, 6,7-H's), 4.83, 5.16 (each s, 19-H's), 3.73–4.3 (m, 1,3-H's), 2.96–3.3 (m, H's adjacent to N), 0.8–1.16 (m, 21-H's, Me H's of ethyl), 0.56 (s, 18-H's).

EXAMPLE 16

1α,3β-Dihydroxy-9,10-secochola-5(Z),7,10(19)-trienic Acid, N-methyl-N-phenyl Amide [Formula (I)—A=(A-2), R$^1$=CH$_3$, R$^2$=Ph, R$^3$=α-CH$_3$, R$^4$=R$^5$=H, X=CH$_2$, Y=CH$_2$, Z=valence bond]

A mixture of 1α,3β-bis-triisopropylsilyloxy-9,10-secochola-5(Z),7,10(19)-trienic acid (175 mg) and dicyclohexylcarbodiimide (52 mg) in dichloromethane (0.75 ml) is stirred at room temperature for 1 hour, then treated with N-methylaniline (27 mg). The resulting mixture is stirred at room temperature overnight, monitoring by TLC—if the initially formed acylimidate has not completely reacted it is possible to add more N-methylaniline (0.5–1 eq.) and stir for a further 10–15 hours. The mixture is then diluted with ether, washed with dilute hydrochloric acid then water, dried and the solvent evaporated. The product is purified by chromatography on silica gel. Desilylation of this product is in Example 14(d) by treatment with tetrabutylammonium fluoride in tetrahydrofuran affords the title product (purified by chromatography if necessary). Alternatively hydrogenation of the silyl ether according to Preparation 1(a), followed by similar desilylation affords 1α,3β-dihydroxy-9,10-secochola-5(Z),7-dienic acid, N-methyl-N-phenyl amide [Formula (I)- A=(A-4), R$^1$=CH$_3$, R$^2$=Ph, R$^3$=α-CH$_3$, R$^4$=R$^5$=H, X=CH$_2$, Y=CH$_2$, Z=valence bond].

EXAMPLE 17

1α,3β-Dihydroxy-20-epi-9,10-secochola-5(Z),7,10 (19)-trienic Acid, N-methyl-N-phenyl Amide [Formula (I)—A=(A-2), R$^1$=CH$_3$, R$^2$=Ph, R$^3$=β-CH$_3$, R$^4$=R$^5$=H, X=CH$_2$, Y=CH$_2$, Z=valence bond]

A mixture of 1α,3β-bis-triisopropylsilyloxy-20-epi-9,10-secochola-5(Z),7,10(19)-trienic acid (175 mg) and dicyclohexylcarbodiimide (52 mg) in dichloromethane (0.75 ml) is stirred at room temperature for 1 hour, then treated with N-methylaniline (27 mg). The resulting mixture is stirred at room temperature overnight, monitoring by TLC—if the initially formed acylimidate has not completely reacted it is possible to add more N-methylaniline (0.5–1 eq.) and stir for a further 10–15 hours. The mixture is then diluted with ether, washed with dilute hydrochloric acid then water, dried and the solvent evaporated. The product is purified by chromatography on silica gel. Photosensitized isomerisation of this product as described in Example 14(c) using phenazine in benzene, followed by desilylation as in Example 14(d) by treatment with tetrabutylammonium fluoride in tetrahydrofuran affords the title product (purified by chromatography if necessary). Alternatively hydrogenation of the silyl ether according to Preparation 1(a), followed by similar desilylation affords 1α,3β-dihydroxy-20-epi-9,10-secochola-5(E), 7-dienic acid, N-methyl-N-phenyl amide [Formula (I)—A=(A-5), R$^1$=CH$_3$, R$^2$=Ph, R$^3$ β-CH$_3$, R$^4$=R$^5$=H, X=CH$_2$, Y=CH$_2$, Z=valence bond].

We claim:
1. A compound of the formula (I)

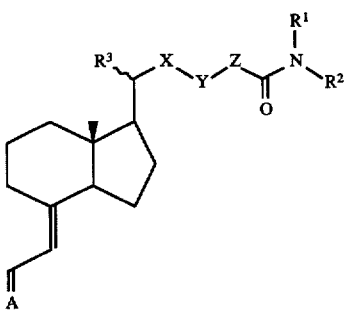

(I)

where $R^1$ and $R^2$, which may be the same or different, each represent a hydrogen atom or an aliphatic, cycloaliphatic, araliphatic or aryl group or together with the nitrogen atom to which they are attached form a heterocyclic group; $R^3$ represents a methyl group having α- or β-configuration; X represents a valence bond or a $C_{1-2}$ alkylene group; Y represents —O—, —S—, —CH$_2$— or —NR— where R is a hydrogen atom or an organic group; Z represents a valence bond or a $C_{1-3}$ alkylene group; and A= represents a cyclohexylidene moiety characteristic of the A-ring of a 1α-hydroxylated vitamin D or analogue thereof, with the proviso that when —X—Y—Z— together represent an alkylene group containing up to 4 carbon atoms A= does not carry an exocyclic methylene group at the 10-position.

2. Compounds of general formula (I) as claimed in claim 1 wherein A= represents one of the groups

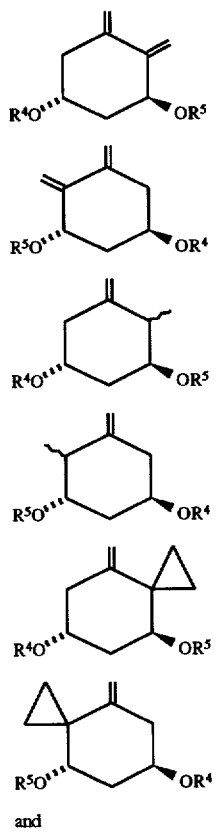

(A-2)

(A-3)

(A-4)

(A-5)

(A-6)

(A-7)

and

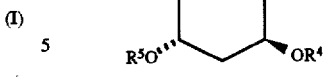

(A-8)

(where $R^4$ and $R^5$, which may be the same or different, each represent a hydrogen atom or an O-protecting group).

3. Compounds of general formula (I) as claimed in claim 2 wherein $R^4$ and $R^5$ represent etherifying silyl groups.

4. Compounds of general formula (I) as claimed in claim 2 wherein $R^4$ and $R^5$ are selected from hydrogen atoms and metabolically labile etherifying or esterifying groups.

5. Compounds of general formula (I) as claimed in claim 1 wherein A= represents one of the groups

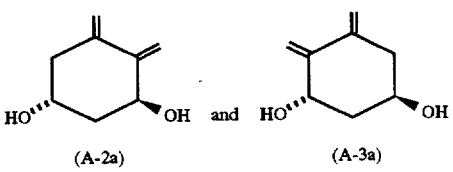

(A-2a)     (A-3a)

6. Compounds of general formula (I) as claimed in claim 1 wherein $R^1$ and $R^2$ are selected from hydrogen atoms, $C_{1-6}$ alkyl groups, $C_{3-8}$ cycloalkyl groups, $C_{6-12}$ aryl $C_{1-4}$ alkyl and optionally substituted $C_{6-12}$ carbocyclic aryl groups.

7. Compounds of general formula (I) as claimed in claim 6 wherein $R^1$ and $R^2$ are selected from hydrogen atoms, $C_{1-6}$ alkyl groups and $C_{3-8}$ cycloalkyl groups.

8. Compounds of general formula (I) as claimed in claim 7 wherein $R^1$ and $R^2$ are selected from hydrogen atoms, methyl, ethyl and cyclopropyl groups.

9. Compounds of general formula (I) as claimed in claim 1 wherein $R^1R^2N$— represents a heterocyclic group comprising one or more 5- and/or 6-membered rings optionally containing one or more further heteroatoms selected from O, N and S.

10. Compounds of general formula (I) as claimed in claim 9 wherein $R^1R^2N$— represents a piperidino group.

11. The use of an active compound of general formula (I) as claimed in claim 1 for the manufacture of a medicament for use in wound healing, suppression of parathyroid hormone or in the treatment or prophylaxis of neoplastic disease, infection, bone disease, autoimmune disease, host-graft reaction, transplant rejection, inflammatory disease, neoplasia, hyperplasia, myopathy, enteropathy, spondylitic heart disease, dermatological disease, hypertension, rheumatoid arthritis, psoriatic arthritis, secondary hyperparathyroidism or asthma in a human or animal subject.

12. Pharmaceutical compositions comprising an active compound of general formula (I) as claimed in claim 1 in admixture with one or more physiologically acceptable carriers or excipients.

13. A method of treatment of a human or animal subject to promote wound healing or suppression of parathyroid hormone or to combat neoplastic disease, infection, bone disease, autoimmune disease, host-graft reaction, transplant rejection, inflammatory disease, neoplasia, hyperplasia, myopathy, enteropathy, spondylitic heart disease, dermatological disease, hypertension, rheumatoid arthritis, psoriatic arthritis, secondary hyperparathyroidism or asthma, comprising administration to said subject of an effective amount of an active compound of general formula (I) as claimed in claim 1.

14. A process for the preparation of a compound of general formula (I) as defined in claim 1 which comprises either:

A) isomerising a 5,6-trans isomer of general formula (I) to a corresponding 5,6-cis isomer, followed if necessary and/or desired by removal of any O-protecting groups;

B) hydroxylating a 1-unsubstituted-5,6-trans analogue of a compound of general formula (I) to prepare a 5,6-trans isomer of general formula (I), followed if necessary and/or desired by isomerisation and/or removal of any O-protecting group;

C) reacting a compound containing a precursor for the desired 17-position side chain in one or more stages and with one or more reactants serving to form the desired side chain, followed if necessary and/or desired by isomerisation and/or removal of any O-protecting groups; or D) reacting a compound of formula (I) to modify the substitution pattern about the A= group, followed if necessary and/or desired by isomerisation and/or removal of protecting groups.

* * * * *